United States Patent
Bennani et al.

(10) Patent No.: US 7,718,647 B2
(45) Date of Patent: *May 18, 2010

(54) SUBSTITUTED AZEPINE DERIVATIVES AS SEROTONIN RECEPTOR MODULATORS

(75) Inventors: Youssef L. Bennani, Shaker Heights, OH (US); Michael J. Robarge, University Heights, OH (US); David C. Bom, Broadview Heights, OH (US); Norbert Varga, Cleveland Heights, OH (US); Lawrence N. Tumey, Fairview Park, OH (US)

(73) Assignee: Athersys, Inc., Cleveland, OH (US)

( * ) Notice: Subject to any disclaimer, the term of this patent is extended or adjusted under 35 U.S.C. 154(b) by 1169 days.

This patent is subject to a terminal disclaimer.

(21) Appl. No.: 11/170,266

(22) Filed: Jun. 29, 2005

(65) Prior Publication Data

US 2006/0003990 A1 Jan. 5, 2006

Related U.S. Application Data

(60) Provisional application No. 60/584,916, filed on Jun. 30, 2004.

(51) Int. Cl.
*A61P 25/00* (2006.01)
*A61K 31/55* (2006.01)
*C07D 223/16* (2006.01)

(52) U.S. Cl. .................................. 514/215; 540/593

(58) Field of Classification Search ................ 514/215; 540/593

See application file for complete search history.

(56) References Cited

U.S. PATENT DOCUMENTS 4,414,225 A * 11/1983 Sauter et al. ................ 514/215
4,575,504 A * 3/1986 Sauter et al. ................ 514/215
4,904,653 A 2/1990 Clark et al.
5,594,004 A 1/1997 Katano et al.
5,998,433 A 12/1999 Takatani et al.
2002/0107278 A1 8/2002 Frank et al.
2004/0209865 A1* 10/2004 Stenkamp et al. ....... 514/217.03

FOREIGN PATENT DOCUMENTS

EP 0488663 A 6/1992
WO 02074746 A 9/2002
WO 2005040169 A 5/2005

OTHER PUBLICATIONS

Frehel et al., New Synthesis of 5,6,7,8-Tetrahydro-4H-thieno/2,3-d]azepine, Journal of Heterocyclic Chemistry, vol. 22, No. 4, pp. 1011-1016, Jul.-Aug. 1985.*
Shue, et al., An Efficient Synthesis of 2-Methyl-5,6,7,8-Tetrahydro-4H-Furo [2,3-d]Azepines, J. Org. Chem. 1991, 56, 2936-2938.
Database Beilstein [Online] Beilstein Institute for Organic Chemistry, Frankfurt-Main, DE; XP002538796, Database accession No. 4667707, 4619769, 4621858, 4660277, 4547247, 1985.
Supplementary European Search Report for corresponding European Application No. EP 05 78 9932 dated Jul. 27, 2009.

* cited by examiner

*Primary Examiner*—Brenda L Coleman
(74) *Attorney, Agent, or Firm*—Wood, Phillips, Katz, Clark & Mortimer

(57) ABSTRACT

The present invention generally relates to a series of compounds, to pharmaceutical compositions containing the compounds, and to use of the compounds and compositions as therapeutic agents. More specifically, compounds of the present invention are hexahydroazepinoindole and octahydroazepinoindole compounds. These compounds are serotonin receptor (5-HT) ligands and are useful for treating diseases, disorders, and conditions wherein modulation of the activity of serotonin receptors (5-HT) is desired (e.g. anxiety, depression and obesity).

5 Claims, No Drawings

SUBSTITUTED AZEPINE DERIVATIVES AS SEROTONIN RECEPTOR MODULATORS

This application claims the benefit of U.S. Provisional Application No. 60/584,916 filed on Jun. 30, 2004.

FIELD OF THE INVENTION

The present invention generally relates to a series of compounds, to pharmaceutical compositions containing the compounds, and to use of the compounds and compositions as therapeutic agents. More specifically, compounds of the present invention are hexahydrothienoazepine and octahydrothienoazepine compounds. These compounds are serotonin receptor (5-HT) ligands and are useful for treating diseases, disorders, and conditions wherein modulation of the activity of serotonin receptors (5-HT) is desired (e.g. addiction, anxiety, depression and obesity).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors (5-HT$_{1-7}$) contain one to seven separate receptors that have been formally classified. See Glennon, et al., *Neuroscience and Behavioral Reviews*, 1990, 14, 35; and D. Hoyer, et al. *Phannacol. Rev.* 1994, 46, 157-203.

For example, the 5-HT$_2$ family of receptors contains 5-HT$_{2a}$, 5-HT$_{2b}$, and 5-HT$_{2c}$ subtypes, which have been grouped together on the basis of primary structure, secondary messenger system, and operational profile. All three 5-HT$_2$ subtypes are G-protein coupled, activate phospholipase C as a principal transduction mechanism, and contain a seven-transmembrane domain structure. There are distinct differences in the distribution of the three 5-HT$_2$ subtypes in a mammal. The 5-HT$_{2b}$ and 5-HT$_{2a}$ receptors are widely distributed in the peripheral nervous system, with 5-HT$_{2a}$ also found in the brain. The 5-HT$_{2c}$ receptor has been found only in the central nervous system, being highly expressed in many regions of the human brain. See G. Baxter, et al. *Trends in Pharmacol. Sci.* 1995, 16, 105-110.

Subtype 5-HT$_{2a}$ has been associated with effects including vasoconstriction, platelet aggregation, and bronchoconstriction, as well as certain CNS effects, while subtype 5-HT$_{2c}$ has been associated with diseases that include depression, anxiety, obsessive compulsive disorder, addiction, panic disorders, phobias, psychiatric syndromes, and obesity. Very little is known about the pharmocologic role of the 5-HT$_{2b}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., 1. *Med. Chem.*, 1998, 41,1598-1612; G. A. Kennett, *Drugs*, 1998, 1, 4, 456-470; and A. Dekeyne, et al., *Neurophannacology,*1999, 38, 415-423.

WO 93/13105 discloses thiophene derivatives; U.S. Pat. No. 4,414,225 discloses thiophene, furan and pyrrole derivatives and WO 96/12201 discloses furan derivatives.

SUMMARY OF THE INVENTION

The present invention is directed to compounds of the formula:

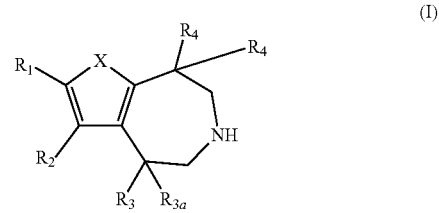

(I)

where X is S, O or NR$_5$;

R$_1$ and R$_2$ are independently selected from the group consisting of H, halogen, C$_{1-8}$ alkyl, C$_{1-8}$ alkylaryl, C$_{1-8}$ alkyl heteroaryl, C$_{1-8}$ alkenyl, perhalo alkyl, CN, OR$_5$, SR$_5$, N(R$_5$)$_2$, CON(R$_5$)$_2$, NR$_5$COR$_5$, NR$_5$CO$_2$R$_5$, SO$_2$N(R$_5$)$_2$, NR$_5$SO$_2$R$_5$, aryl and heteroaryl, wherein said aryl or heteroaryl can be optionally substituted with up to three substituents selected from alkyl, halogen and alkoxy or R$_1$ and R$_2$ taken together form a 5- or 6-member ring;

R$_3$ is selected from the group consisting of H, C$_{1-8}$ alkyl, C$_{1-8}$ alkylaryl, C$_{1-8}$ alkylheteroaryl, OR$_5$, —CH$_2$—O—C$_{1-8}$ alkyl, —CH$_2$OH, —COO—C$_{1-8}$ alkyl, —CON(R$_5$)$_2$, and aryl;

R$_{3a}$ is H or R$_3$ and R$_{3a}$ taken together are —CH$_2$CH$_2$— or R$_2$ and R$_3$ form a 5- or 6-member ring;

R$_4$ is selected from the group consisting of H, C$_{1-8}$ alkyl, C$_{1-8}$ alkylaryl, C$_{1-8}$ alkylheteroaryl, OR$_5$, —CH$_2$—O—C$_{1-8}$ alkyl, —CH$_2$OH, —COO—C$_{1-8}$ alkyl, —CON(R$_5$)$_2$ and aryl;

R$_{4a}$ is H or R$_3$ and R$_{3a}$ taken together are —CH$_2$CH$_2$—; and

R$_5$ is selected from the group consisting of H, C$_{1-8}$ alkyl, C$_{1-8}$ alkylaryl, C$_{1-8}$ alkylheteroaryl, aryl, heteroaryl, and perhaloalkyl or together with the atom to which it is attached, R$_5$ forms a heteroaryl ring.

Another embodiment of the present invention provides a pharmaceutical composition comprising a compound of Formula (I), or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-HT$_{2c}$ receptor is implicated and modulation of a 5-HT$_{2c}$ function is desired. The method comprises administering a therapeutically effective amount of a compound of Formula (I), or a pharmaceutically acceptable salt thereof, to the mammal.

Yet another embodiment of the present invention comprises a method of modulating 5-HT receptor function with an effective amount of compound of Formula (I), or a pharmaceutically acceptable salt thereof.

A further embodiment of the present invention provides a method of treating or preventing diseases, disorders, and/or conditions of the central nervous system. The method comprises administering a therapeutically effective amount of a compound of Formula (I), or a pharmaceutically acceptable salt thereof, to the mammal.

Specific diseases, disorders and/or conditions for which compounds of the Formula (I) may have activity include obesity, depression, schizophrenia, anxiety, obsessive compulsive disorder, addiction, panic disorders, sleep disorders, migraine, Type II diabetes, epilepsy, phobias and phychiatric syndromes.

DETAILED DESCRIPTION OF THE INVENTION

The following definitions are used, unless otherwise described:

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "halo" is defined herein to include fluoro, chloro, bromo, or iodo. Similarly, the term "halogen" is defined herein to include fluorine, chlorine, bromine, and iodine.

The term "amino", alone or in combination, includes the group —$NH_2$ or —$NR_aR_b$, wherein $R_a$ and $R_b$ are independently hydrogen, alkyl, alkylaryl, or aryl.

The term "aryl," alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of HI halo; CN, $NO_2$, $CF_3$, $N_3$, $C_{1-6}$ alkyl, OH, $NR^aR^b$, $OC_{1-6}$ alkyl, $OR^a$, C(=O)$NR^aR^b$, C(=S)$NR^aR^b$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinoliziny1, 4 nH-carbazolyl, acridinyl, benzo[b]thienyl, benzothiazolyl, 13-carbolinyl, carbazolyl, chromenyl, cinnaolinyl, dibenzo [b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, 0, $C_{1-4}$alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "Het" generally represents a heterocyclic group, saturated or partially unsaturated, containing at least one heteroatom selected from the group consisting of oxygen, nitrogen, and sulfur, and optionally substituted with $C_{1-6}$alkyl or C(=O)$OR^6$. Typically "Het" is a monocyclic, bicyclic, or tricyclic group containing one or more heteroatoms selected from the group consisting of oxygen, nitrogen, and sulfur. A "Het" group also can contain an oxo group (=0) attached to the ring. Nonlimiting examples of Het groups include 1,3-dihydrobenzofuran, 1,3-dioxolane,' 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

Preferred embodiments of the present invention include:

Embodiment 1:

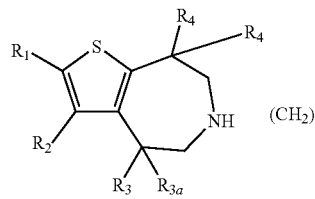

where $R_1$ and $R_2$ are independently selected from the group consisting of H, halogen, $C_{1-8}$ alkyl, $C_{1-8}$ alkylaryl, $C_{1-8}$ alkylheteroaryl, $C_{1-8}$ alkenyl, perhalo alkyl, CN, $OR_5$, $SR_5$, N$(R_5)_2$, CON$(R_5)_2$, $NR_5COR_5$, $NR_5CO_2R_5$, $SO_2N(R_5)_2$, $NR_5SO_2R_5$, aryl and heteroaryl, wherein said aryl or heteroaryl can be optionally substituted with up to three substituents selected from alkyl, halogen and alkoxy or $R_1$ and $R_2$ taken together form a 5- or 6-member ring;

$R_3$ is selected from the group consisting of H, $C_{1-8}$ alkyl, $OR_5$, —$CH_2$—O—$C_{1-8}$ alkyl, —$CH_2OH$, —COO—$C_{1-8}$ alkyl, —CON$(R_5)_2$, and aryl;

$R_{3a}$ is H or $R_3$ and $R_{3a}$ taken together are —$CH_2CH_2$— or $R_2$ and $R_3$ form a 5- or 6-member ring;

$R_4$ is selected from the group consisting of H, $C_{1-8}$ alkyl, $C_{1-8}$ alkylaryl, $C_{1-8}$ alkylheteroaryl, $OR_5$, —$CH_2$—O—$C_{1-8}$ alkyl, —$CH_2OH$, —COO—$C_{1-8}$ alkyl, —CON$(R_5)_2$ and aryl;

$R_{4a}$ is H or $R_3$ and $R_{3a}$ taken together are —$CH_2CH_2$—; and $R_5$ is selected from the group consisting of H, $C_{1-8}$ alkyl, $C_{1-8}$ alkylaryl, $C_{1-8}$ alkylhetroaryl, heteroaryl, and perhaloalkyl or together with the atom to which it is attached, $R_5$ forms a heteroaryl ring.

Embodiment 2:

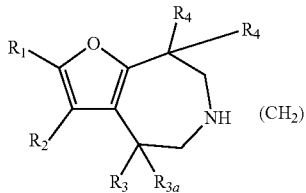

where $R_1$ and $R_2$ are independently selected from the group consisting of H, halogen, $C_{1-8}$ alkyl, $C_{1-8}$ alkylaryl, $C_{1-8}$ alkyl heteroaryl, $C_{1-8}$ alkenyl, perhalo alkyl, CN, $OR_5$, $SR_5$, N$(R_5)_2$, $CON(R_5)_2$, $NR_5COR_5$, $NR_5CO_2R_5$, $SO_2N(R_5)_2$, $NR_5SO_2R_5$, aryl and heteroaryl, wherein said aryl or heteroaryl can be optionally substituted with up to three substituents selected from alkyl, halogen and alkoxy or $R_1$ and $R_2$ taken together form a 5- or 6-member ring;

$R_3$ is selected from the group consisting of H, $C_{1-8}$ alkyl, $C_{1-8}$ alkylaryl, $C_{1-8}$ alkylheteroaryl, $OR_5$, —$CH_2$—O—$C_{1-8}$ alkyl, —$CH_2OH$, —COO—$C_{1-8}$ alkyl, —$CON(R_5)_2$, and aryl;

$R_{3a}$ is H or $R_3$ and $R_{3a}$ taken together are —$CH_2CH_2$— or $R_2$ and $R_3$ form a 5- or 6-member ring;

$R_4$ is selected from the group consisting of H, $C_{1-8}$ alkyl, $C_{1-8}$ alkylaryl, $C_{1-8}$ alkylheteroaryl, $OR_5$, —$CH_2$—O—$C_{1-8}$ alkyl, —$CH_2OH$, —COO—$C_{1-8}$ alkyl, —$CON(R_5)_2$ and aryl;

$R_{4a}$ is H or $R_3$ and $R_{3a}$ taken together are —$CH_2CH_2$—; and $R_5$ is selected from the group consisting of H, $C_{1-8}$ alkyl, $C_{1-8}$ alkylaryl, aryl, $C_{1-8}$ alkylhetroaryl, heteroaryl, and perhaloalkyl or together with the atom to which it is attached, $R_5$ forms a heteroaryl ring.

Embodiment 3:

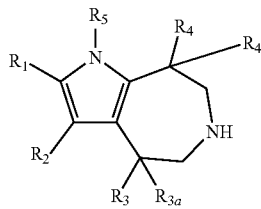

where $R_1$ and $R_2$ are independently selected from the group consisting of H, halogen, $C_{1-8}$ alkyl, $C_{1-8}$ alkylaryl, $C_{1-8}$ alkylheteroaryl, $C_{1-8}$ alkenyl, perhalo alkyl CN, $OR_5$, $SR_5$, N$(R_5)_2$, $CON(R_5)_2$, $NR_5COR_5$, $NR_5CO_2R_5$, $SO_2N(R_5)_2$, $NR_5SO_2R_5$, aryl and heteroaryl, wherein said aryl or heteroaryl can be optionally substituted with up to three substituents selected from alkyl, halogen and alkoxy or $R_1$ and $R_2$ taken together form a 5- or 6-member ring;

$R_3$ is selected from the group consisting of H, $C_{1-8}$ alkyl, $C_{1-8}$ alkylaryl, $C_{1-8}$ alkylheteroaryl, $OR_5$, —$CH_2$—$O$—$C_{1-8}$ alkyl, —$CH_2OH$, —COO—$C_{1-8}$ alkyl, —$CON(R_5)_2$, and aryl;

$R_{3a}$ is H or $R_3$ and $R_{3a}$ taken together are —$CH_2CH_2$— or $R_2$ and $R_3$ form a 5- or 6-member ring;

$R_4$ is selected from the group consisting of H, $C_{1-8}$ alkyl, $C_{1-8}$ alkylaryl, $C_{1-8}$ alkyl heteroaryl, $OR_5$, —$CH_2$—O—$C_{1-8}$ alkyl, —$CH_2OH$, —COO—$C_{1-8}$ alkyl, —$CON(R_5)_2$ and aryl;

$R_{4a}$ is H or $R_3$ and $R_{3a}$ taken together are —$CH_2CH_2$—; and $R_5$ is selected from the group consisting of H, $C_{1-8}$ alkyl, $C_{1-8}$ alkylheteroaryl, $C_{1-8}$ alkylaryl, aryl, heteroaryl, and perhaloalkyl or together with the atom to which it is attached, $R_5$ forms a heteroaryl ring.

Preferably X is S;

$R_1$ is selected from the group consisting of halogen, $C_{1-8}$ alkyl, $OR_5$, $SO_2N(R_5)_2$ and perhaloalkyl;

$R_2$ is selected from the group consisting of hydrogen, halogen, $C_{1-8}$ alkyl and $OR_5$, or together with $R_3$ forms a 5-membered ring;

$R_3$ is hydrogen or $C_{1-8}$ alkyl;

$R_3$ is hydrogen;

$R_4$ is hydrogen or $C_{1-8}$ alkyl;

$R_4$ is hydrogen; and $R_5$ is hydrogen or $C_{1-8}$ alkyl or, together with the atom to which it is attached form a heteroaryl ring.

Presently preferred compounds include
5,6,7,8-Tetrahydro-4H-thieno[2,3-d]azepine;
2-Bromo-5,6,7,8-tetrahydro-4H-thieno[2,3-d]azepine;
2-Chloro-5,6,7,8-tetrahydro-4H-thieno[2,3-d]azepine;
2,3-Dibromo-5,6,7,8-tetrahydro-4H-thieno[2,3-d]azepine;
2,3-Dichloro-5,6,7,8-tetrahydro-4H-thieno[2,3-d]azepine;
2-Bromo-3-chloro-5,6,7,8-tetrahydro-4H-thieno[2,3-d]azepine;
(R,S)5,6,7,8-Tetrahydro-4H-thieno[2,3-d]azepin-4-ol;
2-Chloro-4-methoxy-5,6,7,8-tetrahydro-4H-thieno[2,3-d]azepine;
2-Chloro-4-methyl-5,6,7,8-tetrahydro-4H-thieno[2,3-d]azepine;
2,3-Dichloro-4-methyl-5,6,7,8-tetrahydro-thieno[2,3-d]azepine;
2-(4-Trifluoromethoxy-phenyl)-5,6,7,8-tetrahydro-4H-thieno[2,3-]azepine;
2-(3-Trifluoromethyl-phenyl)-5,6,7,8-tetrahydro-4H-thieno[2,3-d]azepine;
2-(2-Trifluoromethyl-phenyl)-5,6,7,8-tetrahydro-4H-thieno[2,3-d]azepine;
2-(4-Fluoro-phenyl)-5,6,7,8-tetrahydro-4H-thieno[2,3-d]azepine;
2-(2,5-Difluoro-phenyl)-5,6,7,8-tetrahydro-4H-thieno[2,3-d]azepine;
2-(3-Chloro-4-fluoro-phenyl)-5,6,7,8-tetrahydro-4H-thieno[2,3-d]azepine;
2-(2,5-Dichloro-phenyl)-5,6,7,8-tetrahydro-4H-thieno[2,3-d]azepine;
2-(5-Fluoro-2-methoxy-phenyl)-5,6,7,8-tetrahydro-4H-thieno[2,3-d]azepine;
2-(3,4,5-Trimethoxy-phenyl)-5,6,7,8-tetrahydro-4H-thieno[2,3-d]azepine;
2-(4-Ethoxy-phenyl)-5,6,7,8-tetrahydro-4H-thieno[2,3-d]azepine;
2-(4-Ethyl-phenyl)-5,6,7,8-tetrahydro-4H-thieno[2,3-d]azepine;
2-(3-Methoxy-phenyl)-5,6,7,8-tetrahydro-4H-thieno[2,3-d]azepine;
2-Phenyl-5,6,7,8-tetrahydro-4H-thieno[2,3-d]azepine;
2-(3-Fluoro-biphenyl-4-yl)-5,6,7,8-tetrahydro-4H-thieno[2,3-d]azepine;
2-(2-Fluoro-biphenyl-4-yl)-5,6,7,8-tetrahydro-4H-thieno[2,3-d]azepine;
2-Bromo-3-methyl-5,6,7,8-tetrahydro-4H-thieno[2,3-d]azepine;

2-Bromo-3-methoxy-5,6,7,8-tetrahydro-4H-thieno[2,3-d]
azepine;
2-Bromo-4-methyl-5,6,7,8-tetrahydro-4H-thieno[2,3-d]
azepine;
2-Bromo-8-methyl-5,6,7,8-tetrahydro-4H-thieno[2,3-d]
azepine;
2-(Pyrrolidine-1-sulfonyl)-5,6,7,8-tetrahydro-4H-thieno[2,
3-d]azepine;
5,6,7,8-Tetrahydro-4H-thieno[2,3-d]azepine-2-sulfonic acid
dimethylamide;
3-Methyl-5,6,7,8-tetrahydro-4H-thieno[2,3-d]azepine-2-
sulfonic acid dimethylamide;
2-Bromo-4,4a,5,6,7,8-hexadydro-3H-1-thia-6-aza-cyclo-
penta[cd]azulene;
2-Methyl-4,4a,5,6,7,8-hexahydro-3H-1-thia-6-aza-cyclo-
penta[cd]azulene;
Trifluoromethyl-5,6,7,8-tetrahydro-4H-thieno[2,3-d]
azepine;
3-Bromo-2-trifluoromethyl-5,6,7,8-tetrahydro-4H-thieno[2,
3-d]azepine;
2-tert-Butyl-3-methoxy-5,6,7,8-tetrahydro-4H-thieno[2,3]
d]azepine;
2-Naphthalene-1-yl-5,6,7,8-tetrahydro-4H-thieno[2,3-d]
azepine;
2-Naphthalene-2-yl-5,6,7,8-tetrahydro-4H-thieno[2,3-d]
azepine;
2-(2,6-Difluoro-phenyl)-5,6,7,8-tetrahydro-4H-thieno[2,3-
d]azepine;
3-(2,6-Difluoro-phenyl)-5,6,7,8-tetrahydro-4H-thieno[2,3-
d]azepine;
2-(2-Chloro-6-fluoro-benzyl)-5,6,7,8-tetrahydro-4H-thieno
[2,3-d]azepine;
3-Bromo-2-(2-chloro-6-fluoro-benzyl)-5,6,7,8-tetrahydro-
4H-thieno[2,3-d]azepine;
2-Amino-5,6,7,8-tetrahydro-4H-thieno[2,3-d]azepine-3-
carboxylic acid ethyl ester;
2-Amino-5,6,7,8-tetrahydro-4H-thieno[2,3-c]azepine-3-car-
boxylic acid ethyl ester;
5,6,7,8-Tetrahydro-4H-thieno[2,3-d]azepine-3-carboxylic
acid ethyl ester; and
5,6,7,8-Tetrahydro-4H-thieno[2,3-c]azepine-3-carboxylic
acid ethyl ester.
Particularly preferred compounds include:
5,6,7,8-Tetrahydro-4H-thieno[2,3-d]azepine;
2,3-Dichloro-5,6,7,8-tetrahydro-4H-thieno[2,3-d]azepine;
2-Bromo-3-chloro-5,6,7,8-tetrahydro-4H-thieno[2,3-d]
azepine;
2-Bromo-3-methyl-5,6,7,8-tetrahydro-4H-thieno[2,3-d]
azepine;
2-Bromo-3-methoxy-5,6,7,8-tetrahydro-4H-thieno[2,3-d]
azepine;
2-Bromo-4-methyl-5,6,7,8-tetrahydro-4H-thieno[2,3-d]
azepine;
2-Bromo-8-methyl-5,6,7,8-tetrahydro-4H-thieno[2,3-d]
azepine;
2-(Pyrrolidine-1-sulfonyl)-5,6,7,8-tetrahydro-4H-thieno[2,
3-d]azepine;
5,6,7,8-Tetrahydro-4H-thieno[2,3-d]azepine-2-sulfonic acid
dimethylamide;
3-Methyl-5,6,7,8-tetrahydro-4H-thieno[2,3-d]azepine-2-
sulfonic acid dimethylamide;
2-Bromo-4,4a,5,6,7,8-hexadydro-3H-1-thia-6-aza-cyclo-
penta[cd]azulene;
2-Methyl-4,4a,5,6,7,8-hexahydro-3H-1-thia-6-aza-cyclo-
penta[cd]azulene;
Trifluoromethyl-5,6,7,8-tetrahydro-4H-thieno[2,3-d]
azepine;

3-Bromo-2-trifluoromethyl-5,6,7,8-tetrahydro-4H-thieno[2,
3-d]azepine; and
2-tert-Butyl-3-methoxy-5,6,7,8-tetrahydro-4H-thieno[2,3]
d]azepine.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphdrsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbet acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfumingagents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The compounds of the present invention may be prepared by the procedures set forth in Schemes. The general analytical conditions set forth were utililized in all examples.

General Analytical Conditions:

HPLC analysis and purification was performed using a Waters 2525 binary gradient pump, Waters 2767 sample manager, Waters 2487 UV detector (220 and 254 nM), and Waters Micromass ZQ electrospray mass spec detector. The Micromass ZQ was set for both positive and negative ionization (cone voltage=25 and 50, respectively). Analytical HPLC analysis was performed as follows:

Waters XTerra MS C18 50×4.6 mm 3.5 μm column

Mobile Phase: 10 mM Ammonium Acetate buffer at pH 5.75 and Acetonitrile

Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was performed as follows:

Waters XTerra Prep MS C18 50×19 mm 5 μm column

Mobile Phase: 10 mM Ammonium Acetate buffer at pH 5.75 and Acetonitrile

Acetonitrile: 10 to 99% at 8 minutes, 99% hold to 9 minutes, 99 to 10% at 9.5 minutes, re-equilibrate NMR analysis was performed using a Bruker BioSpin UltraShield NMR (300 MHz)

Scheme 1a:
Synthesis of trifluoromethyl and monohalogenated thienylazepines.

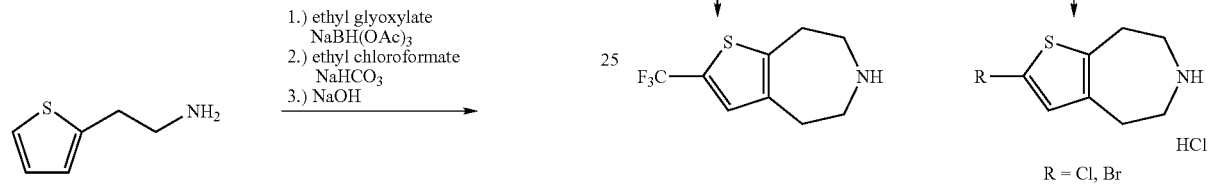

Scheme 1b:
Synthesis of dihalogenated and 3-bromo-2-trifluoromethyl-thienylazepines.

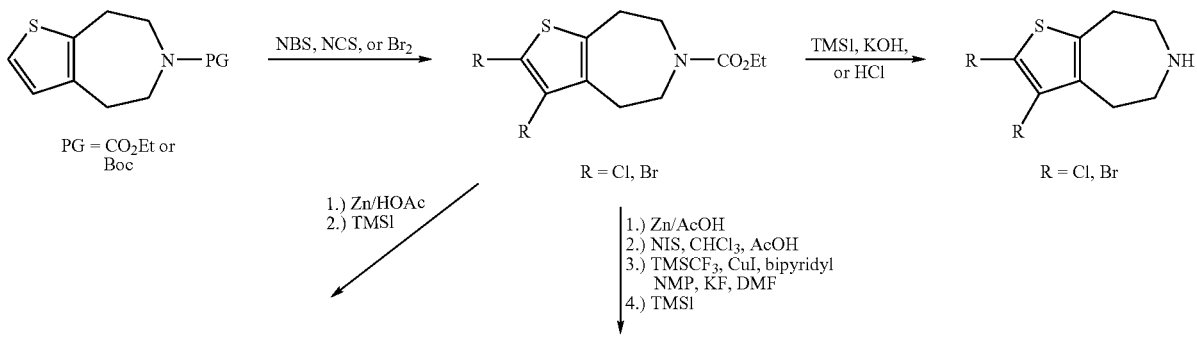

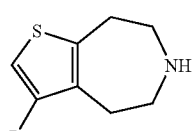

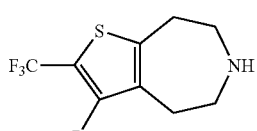

R = Cl, Br

Scheme 2:
Synthesis of biaryl thienylazepines.

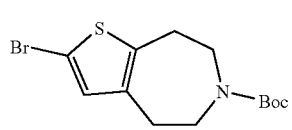

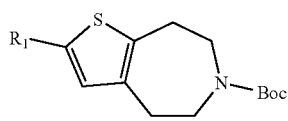

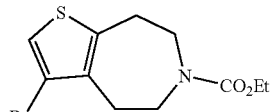

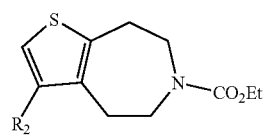

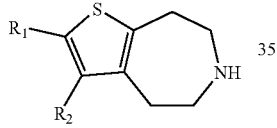

R$_1$ = H, Cl, Br
R$_2$ = aryl, heteroaryl, vinyl

Scheme 3:
Synthesis of alkyl and benzyl thienylazapines analogs.

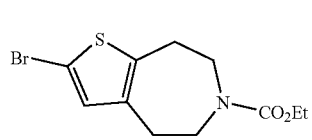

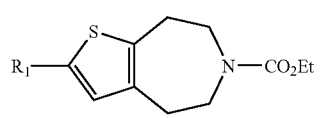

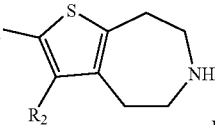

R$_1$ = aryl, heteroaryl, vinyl
R$_2$ = H, Cl, Br

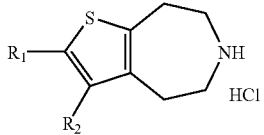

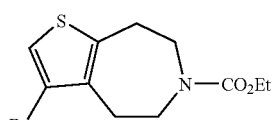

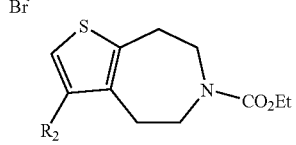

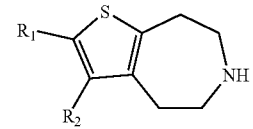

R$_1$ = H, Cl, Br
R$_2$ = alkyl, benzyl

R$_1$ = alkyl, benzyl
R$_2$ = H, Cl, Br

Scheme 4.
Synthesis of 2-bromo-3-methyl thienylazepine and 2,3-dichlorothienylazepine and related analogs.

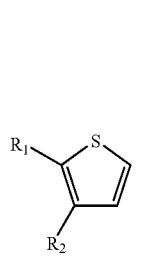

R$_1$ = Br, R$_2$ = CH$_3$
R$_1$ = Cl, R$_2$ = Cl

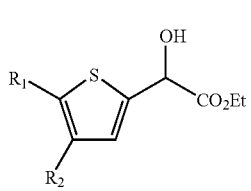

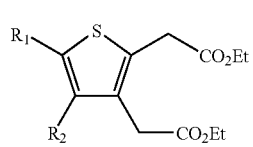

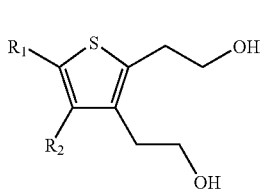

-continued
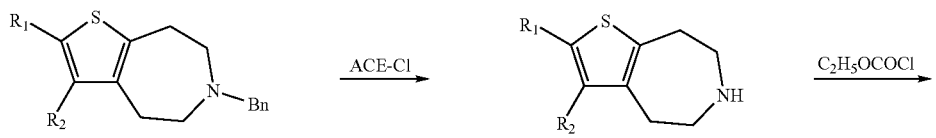
$R_1$ = Br, $R_2$ = $CH_3$
$R_1$ = Cl, $R_2$ = Cl
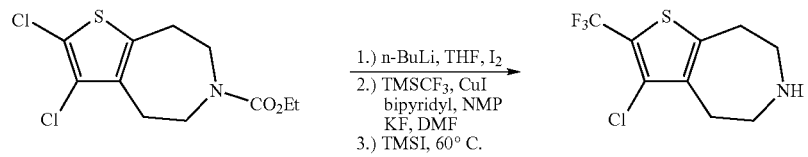
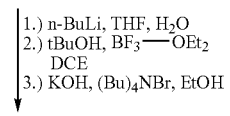
R = t-Bu, t-BuCH$_2$(CH$_3$)$_2$C, H
Scheme 5.
Synthesis of 3-Methoxy thienylazepines
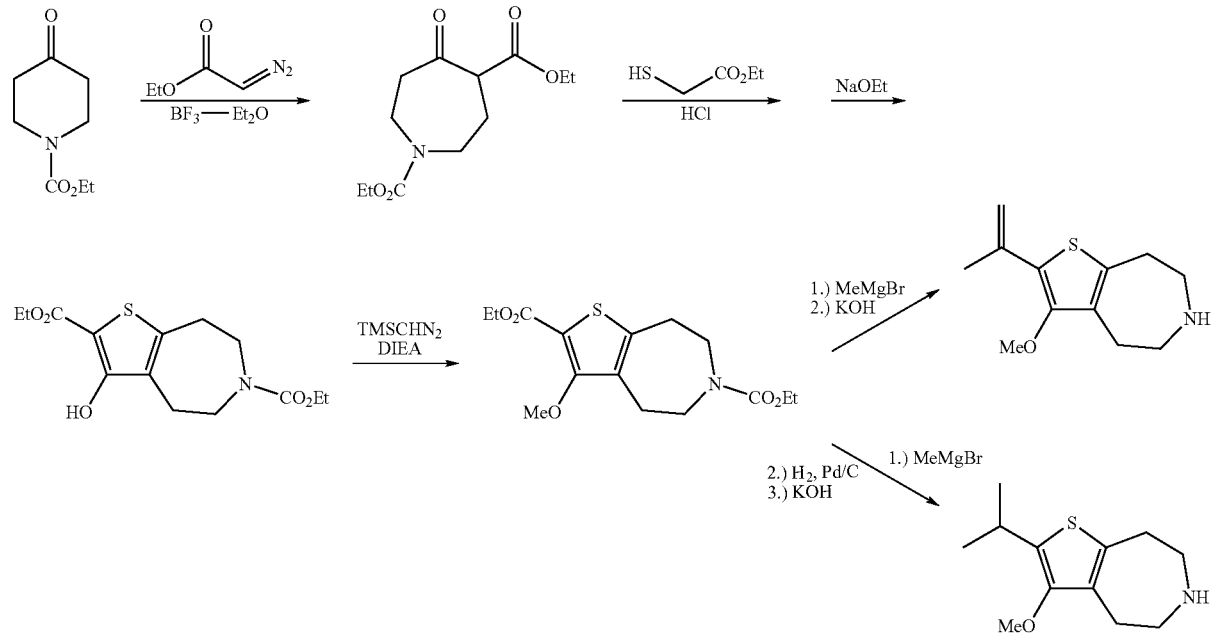

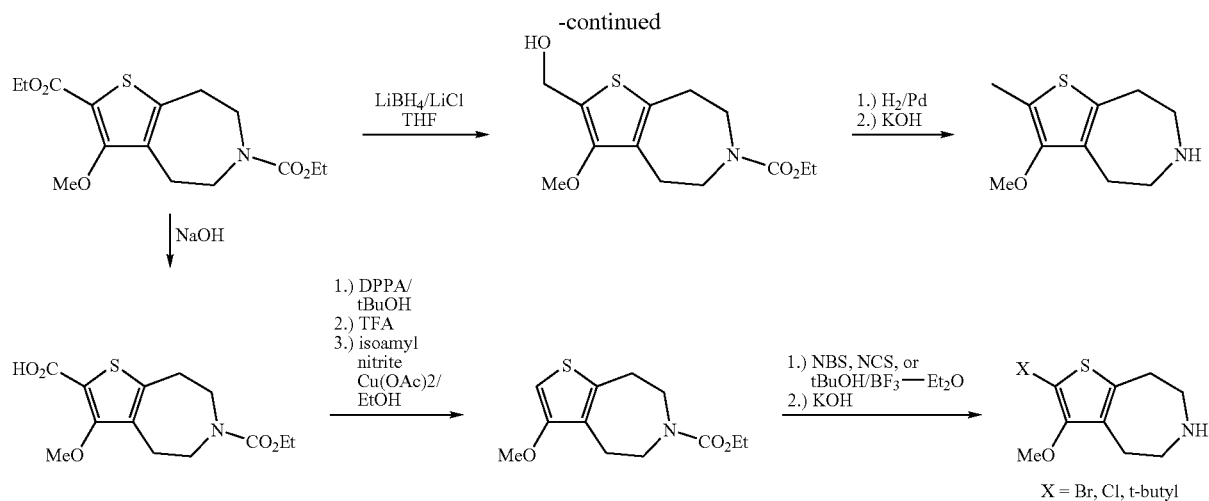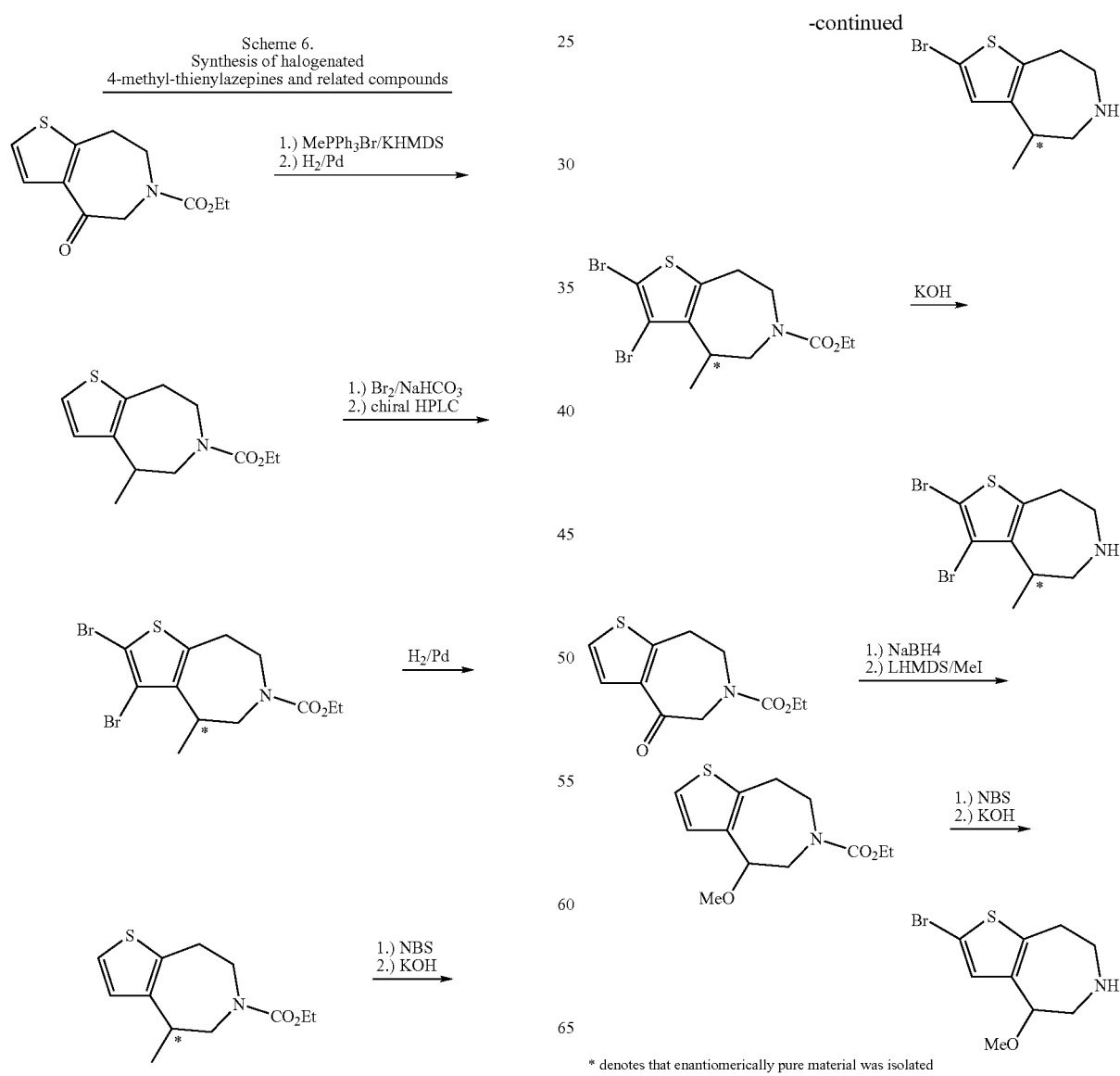
* denotes that enantiomerically pure material was isolated

Scheme 7.
Synthesis of halogenated 8-methyl-thienylazepines and related compounds
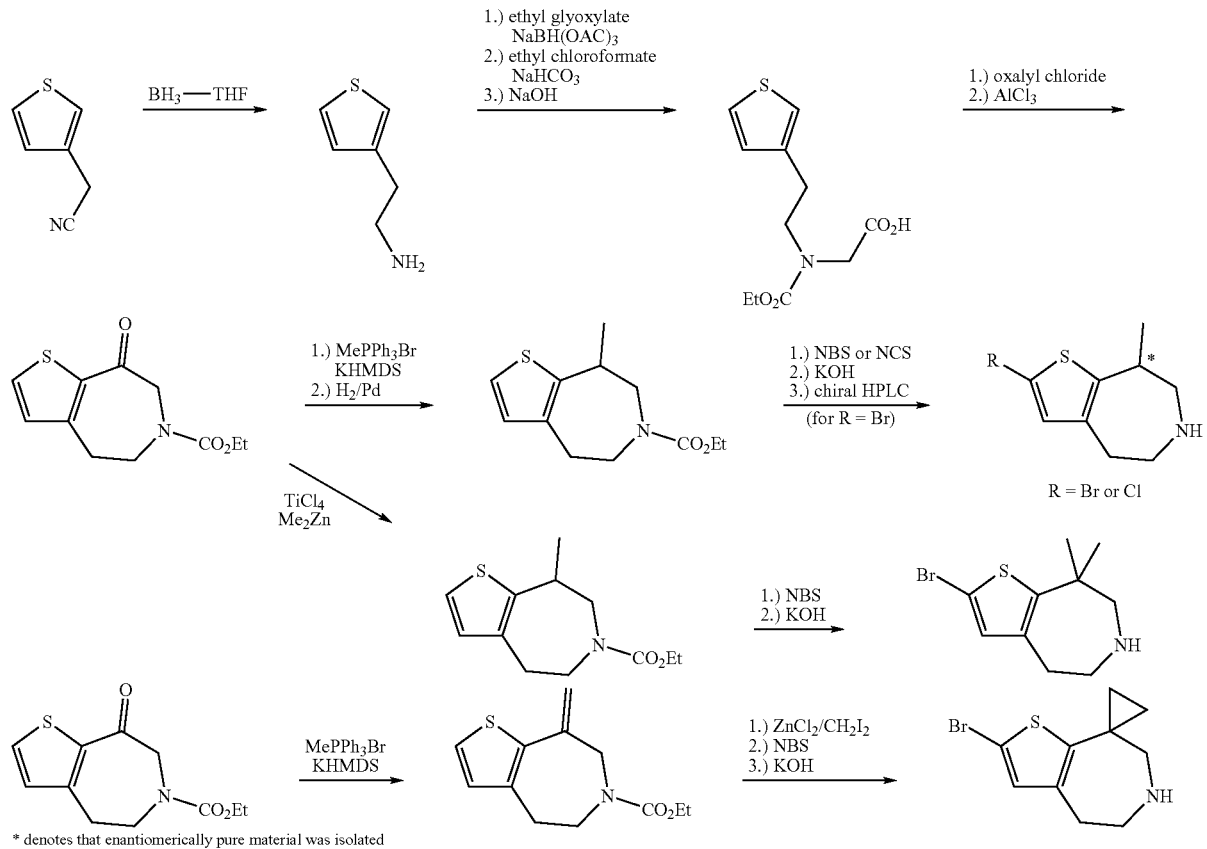
Scheme 8.
Synthesis of 2-sulfonamido- and 2-amido-thienylazepines.
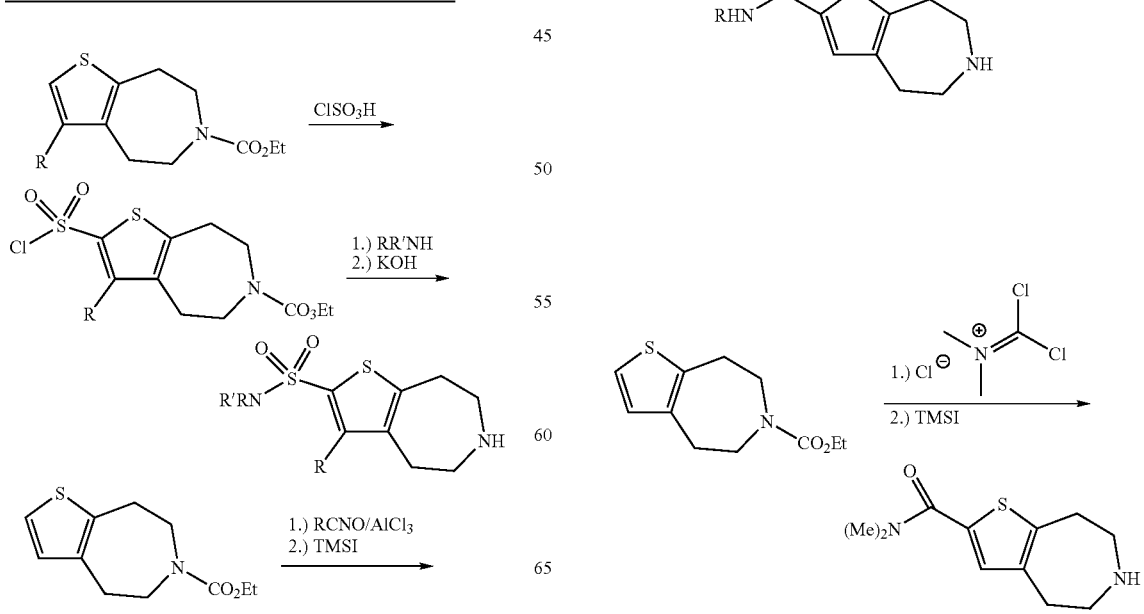

Scheme 9: Synthesis of 3-alkyl thienylazapines and related analogs
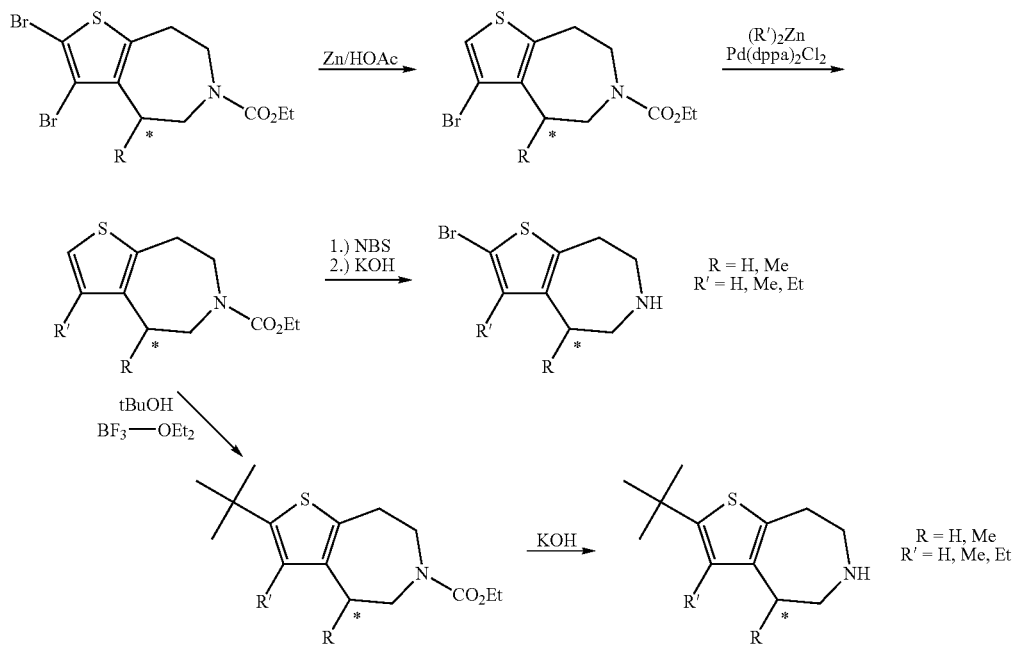
Scheme 10:
Synthesis of tricyclic thiophene azepine derivatives
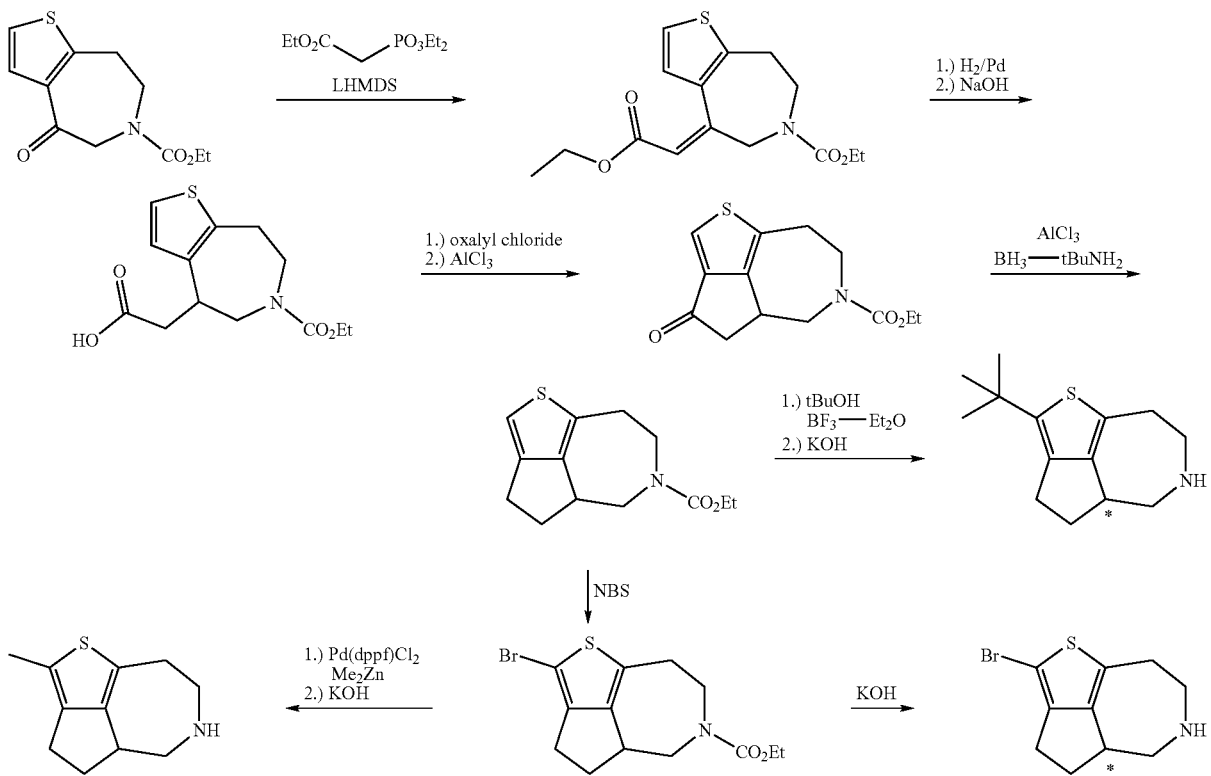
*denotes that enantiomerically pure material was isolated Scheme 11:
Synthesis of furanylazepines

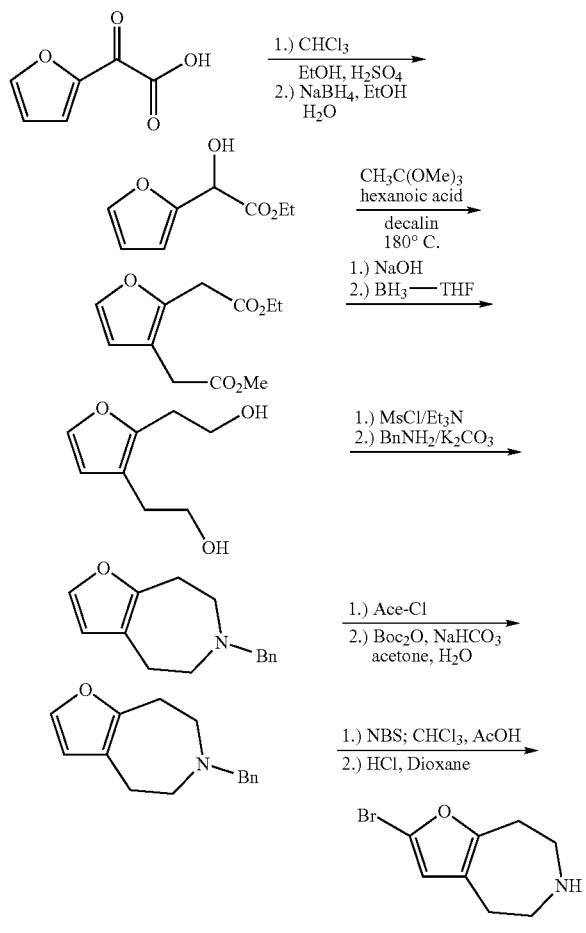

EXAMPLE 1

2-Bromo-5,6,7,8-tetrahydro-4H-thieno[2,3-d]azepine
(Scheme 1a)

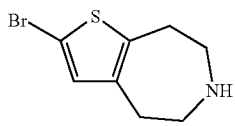

a.) [Ethoxycarbonyl-(2-thiophen-2-yl-ethyl)-amino]-acetic acid ethyl ester

2-Thiophen-2-yl-ethylamine (21 g, 165 mmol) was stirred in 1 liter of DCM. Ethyl glyoxylate (165 mmol, 50% in toluene) was added followed by 50 uL HOAc. The reaction was stirred for 10 minutes after which time NaBH(OAc)$_3$ (214 mmol, 45 g) was added slowly. After 15 minutes HOAc was added (214 mmol) and the reaction was stirred for 20 minutes. The reaction was concentrated and the crude material was dissolved in 500 mL each of THF and water. NaHCO$_3$ (42 g, 500 mmol) was added followed by ethyl chloroformate (21 mL, 214 mmol). Saturated NaHCO$_3$ was added slowly to the reaction until the gas evolution was minimal. After stirring overnight, the reaction was diluted with EtOAc (400 mL). The product was extracted 2× into EtOAc, dried over MgSO$_4$, and concentrated to give the subtitle product as a dark oil that was used without further purification.

b.) [Ethoxycarbonyl-(2-thiophen-2-yl-ethyl)-amino]-acetic acid

The crude material from step a) (~165 mmol) was dissolved in EtOH (700 mL) and treated with 600 mL of 1M NaOH. After stirring overnight, the reaction was acidified with concentrated HCl to pH~1. The crude reaction was diluted with EtOAc (400 mL) and washed with water. The water was back-extracted with EtOAc. The combined organic extracts were washed with water (2×) and dried over MgSO$_4$. Concentration and evaporation from toluene (2×) gave the subtitle product as a solid, which was used without further purification.

c.) 4-Oxo-4,5,7,8-tetrahydro-thieno[2,3-d]azepine-6-carboxylic acid ethyl ester

The product of step b) (~165 mmol) was dissolved in 1 L of DCM. DMF (100 uL) was added followed slowly by oxalyl chloride (21.7 mL, 247 mmol). After 1 hour the reaction was concentrated to dryness and the crude material was re-dissolved in DCE (1 L). AlCl$_3$ (55 g, 410 mmol) was carefully added and the reaction was stirred at room temperature for ½ hour. The crude reaction was quenched with ice, diluted with EtOH (300 mL), washed with water (3×), and dried over MgSO$_4$. The title product was purified by silica gel chromatography (30% EtOAc in Hexanes) to give 10.5 g of the subtitle compound as an off-white solid. MS: ESI (positive): 240 (M+H).

d.) 4,5,7,8-Tetrahydro-thieno[2,3-d]azepine-6-carboxylic acid ethyl ester

AlCl$_3$ (3.95 g, 29.7 mmol) was added to 50 mL DCM at 0° C. Borane-t-butyl amine complex (5.2 g, 59.5 mmol) was added followed by the product of step c) (2.37 g, 9.9 mmol) dissolved in DCM (50 mL). The reaction was stirred for 2 hours at room temperature after which time another 3.95 g (29.7 mmol) of AlCl$_3$ was added. After stirring 10 minutes, the reaction was quenched carefully with 0.1 M HCl (~50 mL). After concentration of the organic solvent, the crude reaction mixture was partitioned between 1M HCl and EtOAc (70 mL each). The aqueous layer was back extracted 1× EtOAc. The combined organic layers were dried over MgSO$_4$ and concentrated. The subtitle product (1.45 g) was obtained after purification by silica gel chromatography (EtOAc/Hexanes-gradient). $^1$H NMR (300 MHz, CDCl$_3$) 6.96 (d, J=5 Hz, 1H), 6.76 (d, J=5 Hz, 1H), 4.18 (q, J=7 Hz, 2H), 3.52-3.78 (m, 4H), 2.78-3.08 (m, 4H), 1.28 (t, J=7 Hz, 3H). MS: ESI (positive): 226 (M+H).

e.) 5,6,7,8-Tetrahydro-4H-thieno[2,3-d]azepine

The product of step d) (200 mg, 0.89 mmol) was dissolved in 15 mL CHCl$_3$ and treated with TMSI (4.5 mmol, 600 uL). After heating to 70° C. overnight, the reaction was carefully quenched with MeOH (10 mL) and 1 M NaOH (20 mL). The subtitle compound was extracted into DCM (3×20 mL). The extracts were dried over MgSO$_4$ and concentrated to give 178 mg of the subtitle compound. $^1$H NMR (300 MHz, DMSO) 7.20 (d, J=5 Hz, 1H), 6.85 (d, J=5 Hz, 1H), 3.42-3.61 (m, 4H), 2.71-3.03 (m, 4H). MS: ESI (positive): 154 (M+H).

f.) 4,5,7,8-Tetrahydro-thieno[2,3-d]azepine-6-carboxylic acid tert-butyl ester The product of step e) (296 mg, 1.93 mmol) dissolved in a 50:50 mixture of acetone/water (8 mL) was treated with NaHCO$_3$ (340.5 mg, 4.03 mmol) at 0° C. and stirred for 30 minutes. To the resulting solution was added di-tert-butyl dicarbonate (463 mg, 2.12 mmol). The reaction mixture was stirred at ambient temperature for 14 hours. The reaction mixture was poured into water (50 ml) and extracted with EtOAc (3×50 ml). The combined organic phases were washed with brine (75 ml), dried (MgSO$_4$), and concentrated in vacuo to give the crude product as an oil. Purification by silica gel chromatography (EtOAc/Hexane-gradient) gave the subtitled compound as a clear oil; yield (93%). $^1$H NMR (300 MHz, CDCl$_3$) δ 6.96 (d, J=5 Hz, 1H), 6.76 (d, J=5 Hz, 1H), 3.44-3.68 (m, 4H), 2.76-3.06 (m, 4 H), 1.50 (s, 9H). MS: ESI (positive): 254 (M+H).

g.) 2-Bromo-4,5,7,8-tetrahydro-thieno[2,3-d]azepine-6-carboxylic acid tert-butyl ester The product of step f) (10 mg, 0.039 mmol) dissolved in a 50:50 mixture of chloroform/acetic acid (1 ml) was treated with N-bromosuccinimide (7 mg, 0.041 mmol). The reaction mixture was stirred for 30 minutes at ambient temperature. The reaction mixture was poured into water (5 ml) and extracted with CHCl$_3$ (3×5 ml). The combined organic phases were washed with 10% KOH solution (5 ml), brine (5 ml), dried (MgSO$_4$), and concentrated to give the crude product as an oil. Purification by HPLC gave the subtitle compound as an oil. MS: ESI (positive): 332, 334 (M+H).

h.) 2-Bromo-5,6,7,8-tetrahydro-4H-thieno[2,3-d]azepine

The product of step g) (0.39 mmol) dissolved in ether (1 ml) was treated with 4 M HCl/dioxane (1 ml). The reaction mixture was stirred for 18 hours at ambient temperature. The resulting precipitate was filtered and washed with anhydrous diethyl ether to give the title compound as its HCl salt. $^1$H NMR (300 MHz, DMSO) δ 9.40 (s, 2H), 7.05 (s, 1H), 3.14-3.33 (m, 4H), 2.94-3.23 (m, 2H), 2.76-3.06 (m, 2H). MS: ESI (positive): 232, 234 (M+H).

EXAMPLE 2

2-Chloro-5,6,7,8-tetrahydro-4H-thieno[2,3-d]azepine (Scheme 1a)

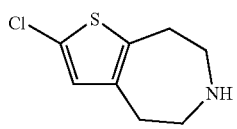

a.) 2-Chloro-4,5,7,8-tetrahydro-thieno[2,3-d]azepine-6-carboxylic acid tert-butyl ester The product of Example 1, step f) (10 mg, 0.039 mmol, Example 1) in CHCl$_3$ (1 ml) and HOAc (1 mL) was treated with N-chlorsuccinimide (6 mg, 0.041 mmol). The reaction mixture was stirred for 12 hours at ambient temperature. The reaction mixture was poured into water (5 ml) and extracted with CHCl$_3$ (3×5 ml). The combined organic phases were washed with 10% KOH solution (5 ml), brine (5 ml), dried (MgSO$_4$), and concentrated to give the crude product as an oil. Purification by HPLC gave the subtitled compound as a clear oil. MS: ESI (positive): 288 (M+H).

b.) 2-Chloro-5,6,7,8-tetrahydro-4H-thieno[2,3-d]azepine

The title compound was prepared by the method of Example 1 step h), using the product of step a). $^1$H NMR (300 MHz, DMSO) δ 6.72 (s, 2H), 2.78-2.85 (m, 2H), 2.72-2.79 (m, 4H), 2.51-2.70 (m, 2H). MS: ESI (positive): 188 (M+H).

EXAMPLE 3

2,3-Dibromo-5,6,7,8-tetrahydro-4H-thieno[2,3-d]azepine (Scheme 1b)

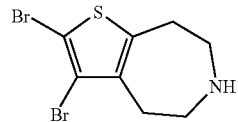

a.) 2,3-Dibromo-4,5,7,8-tetrahydro-thieno[2,3-d]azepine-6-carboxylic acid ethyl ester The product of Example 1, step d) (95 mg, 0.42 mmol) was dissolved in CHCl$_3$ (1 ml) and HOAc (1 mL) and treated with NBS (66.7 mg, 0.42 mmol). The reaction mixture was stirred for 20 minutes at ambient temperature. To this mixture was added sodium acetate (138 mg, 1.68 mmol) and additional NBS (133.4 mg, 0.84 mmol). The reaction mixture was stirred at 60° C. until the reaction was complete as determined by LC/MS. The reaction mixture was cooled to ambient temperature, diluted with saturated sodium bicarbonate (2 ml), and extracted with CHCl$_3$ (3×2 ml). The combined organic phases were washed with brine (10 ml), dried (MgSO$_4$), and concentrated in vacuo to give the product as a crude oil. Purification by flash chromatography (EtOAc/Hexane-gradient) provided the subtitled compound as an oil. MS: ESI (positive): 384 (M+H).

b.) 2,3-Dibromo-5,6,7,8-tetrahydro-4H-thieno[2,3-d]azepine

The product of step b) (0.42 mmol) was dissolved in DCM (2 ml) and treated with iodotrimethylsilane (0.46 mmol). The reaction mixture was stirred at reflux for 24 hours. The reaction mixture was poured into saturated sodium bicarbonate (10 ml) and extracted with dichloromethane (3×5 ml). The combined organic phases were washed with brine (10 ml), dried (MgSO$_4$), and concentrated in vacuo to give an oil.

Purification by preparative HPLC provided the title compound. $^1$H NMR (300 MHz, CDCl$_3$) δ 2.94-3.05 (m, 4H), 2.85-2.92 (m, 4H), 1.92 (s, 1H). MS: ESI (positive): 312 (M+H).

EXAMPLE 4

2,3-Dichloro-5,6,7,8-tetrahydro-4H-thieno[2,3-d]azepine (Scheme 4)

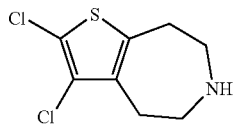

a.) (4,5-Dichloro-thiophen-2-yl)-oxo-acetic acid ethyl ester

At 5-10° C., Chloro-oxo-acetic acid ethyl ester (5.43 ml, 48.7 mmol) was added to 2,3-Dichlorothiophene (5 g, 32.6 mmol). A solution of AlCl$_3$ (6.49 g, 48.7 mmol) dissolved in nitromethane (13 ml) was added dropwise such that the internal reaction temperature did not rise above 10° C. After 1 hour, the reaction mixture was poured into ice water and extracted with CH$_2$Cl$_2$ (2×100 ml). The organic layer was washed with 10% NaHCO$_3$ (2×50 ml), water (1×50 ml) and brine (1×50 ml). Drying (Na$_2$SO$_4$) and concentration provided a light orange solid that was purified by silica gel chromatography (EtOAc/hexane-gradient) providing 6.8 g (82%) of the subtitle compound.

b.) (4,5-Dichloro-thiophen-2-yl)-hydroxy-acetic acid ethyl ester

A solution of the product from step a) (23.0 g, 90.9 mmol) in THF (500 ml) was treated with NaBH(OAc)$_3$ (23.1 g, 109 mmol) and AcOH (250 μl) at 60° C. for 1 hour. The reaction was quenched with AcOH (8 ml) and concentrated to ~250 ml. The contents were diluted with H$_2$O (400 ml) and extracted with CH$_2$Cl$_2$ (1×400 ml; 1×100 ml). The organic layer was dried (MgSO$_4$) and concentrated providing 23 g of the subtitle compound. $^1$H NMR (300 MHz, CDCl$_3$) δ 6.91 (s, 1H); 5.25 (dd, J$_1$=6 Hz, J$_2$=1 Hz, 1H); 4.22-4.40 (m, 2H); 3.52-3.60 (br m, 1H); 1.33 (t, J=7 Hz, 3H).

c.) (4,5-Dichloro-3-methoxycarbonylmethyl-thiophen-2-yl)-acetic acid ethyl ester A solution of the product from step b) (12.2 g, 48.0 mmol) in decalin (145 ml) was treated with trimethylorthoacetate (24.5 ml, 192 mmol) and hexanoic acid (0.61 ml). The flask was equipped with a vigreux column and heated to 180° C. Additional hexanoic acid (3 ml) was periodically added over 6 hours and the reaction was heated overnight. The reaction was concentrated on the rotavap and the residue was extracted with MeOH(100 ml ×2). The MeOH extracts were concentrated and purified by silica gel chromatography (EtOAc/Hexane-gradient) providing 4.36 g (29%) of the subtitle compound. MS: ESI (positive): 311, 313 (M+H).

d.) (3-Carboxymethyl-4,5-dichloro-thiophen-2-yl)-acetic acid

A solution of the product from step c) (1.14 g, 3.66 mmol) in MeOH (7 ml) at 0° C. was treated dropwise with 2M NaOH (3.8 ml). The reaction was warmed to 22° C. and stirred overnight. The solvent was evaporated and the residue was dissolved in 2 M NaOH (50 ml) and extracted with ether (2×50 ml). The basic layer was cooled to 0° C. and acidified to pH 1 with 6 M HCl. The acidic layer was back extracted EtOAc (4×100 ml) and the organic layer was dried (MgSO$_4$) and concentrated. The crude solid was triturated with hexanes and filtered providing 2.75 g (73%) of the subtitle compound. MS: ESI (negative): 267, 269 (M–H).

e.) 2-[4,5-Dichloro-3-(2-hydroxy-ethyl)-thiophen-2-yl]-ethanol

A solution of the product from step d) (2.5 g, 9.33 mmol) in THF (85 ml) was cooled to 0° C. and a 1M solution of BH$_3$-THF (46.6 ml, 46.6 mmol) was added dropwise over 10 minutes. and stirred for an additional 20 minutes after the addition was complete. The reaction was warmed to 22° C. and stirred for 2 hours. The reaction was poured into ice cold sat. NaHCO$_3$ (150 ml) and extracted with EtOAc. The crude was passed through a plug of silica gel washing with EtOAc. Concentration of the eluent provided 1.99 g (88%) of the subtitle compound.

f.) Methanesulfonic acid 2-[4,5-dichloro-2-(2-methanesulfonyloxy-ethyl)-thiophen-3-yl]-ethyl ester A solution of the product from step e) (1.99 g, 8.25 mmol) in CH$_2$Cl$_2$ (41 ml) was cooled to 0° C. and treated with triethylamine (3.4 ml, 24.7 mmol) followed by dropwise addition of methanesulfonyl chloride (1.4 ml, 18.1 mmol) over 10 minutes. After 45 minutes, the crude reaction was diluted with CH$_2$Cl$_2$ (100 ml) and washed with ice water (25 ml), 10% citric acid (2×25 ml), sat. NaHCO$_3$ (2×25 ml) and brine (1×25 ml). The organic layer was dried (MgSO$_4$), concentrated to 20 ml and diluted with anhydrous dioxane (76 ml). This mixture was concentrated to remove remaining CH$_2$Cl$_2$ and the resulting dioxane solution was carried forward to the next reaction.

g.) 6-Benzyl-2,3-dichloro-5,6,7,8-tetrahydro-4H-thieno[2,3-d]azepine

The bismesylate dioxane solution generated in step f) was transferred to a 3-neck reaction flask equipped with a dropping funnel and condenser. Anhydrous potassium carbonate (4.93 g, 35.7 mmol) was added and the contents were heated to reflux. Next, a solution of benzylamine (2.71 g, 25.3 mmol) in anhydrous dioxane (27 ml) was added dropwise over 45 minutes and heating was continued for 16 hours. The salts were filtered off and the solvent was concentrated. The crude was purified by silica gel chromatography (EtOAc/Hexane-gradient) providing 1.43 g (62%) of the subtitle compound. $^1$H NMR (300 MHz, CDCl$_3$) δ 7.20-7.40 (m, 5H); 3.73 (s, 2H); 2.68-2.89 (m, 8H); MS: ESI (positive): 312, 314 (M+H)

h.) 2,3-Dichloro-5,6,7,8-tetrahydro-4H-thieno[2,3-d]azepine Hydrochloride

A solution of the product from step g) (727 mg, 2.33 mmol) in anhydrous dichloroethane (11.6 ml) was cooled to 0° C., treated with 1-Chloroethyl chloroformate (1.27 ml, 11.65 mmol) and the reaction was warmed to 22° C. for 1 hour. The reaction diluted with CH$_2$Cl$_2$ (50 ml) and washed with sat. NaHCO$_3$ (25 ml). The sat. NaHCO$_3$ was back extracted with CH$_2$Cl$_2$ and the combined organic layers were washed with brine (25 ml), dried (MgSO$_4$) and concentrated providing an oily residue, which was taken up in anhydrous MeOH (75 ml) and refluxed for 1 hour. The MeOH was evaporated and the crude residue was triturated with ether and filtered providing 323 mg (54%) of the subtitle compound. $^1$H NMR (300 MHz, DMSO) δ 9.60 (br s, 2H); 3.14-3.28 (m, 6H); 2.97-3.50 (m, 2H); MS: ESI (positive): 222, 224 (M+H).

EXAMPLE 5

2-Bromo-3-chloro-5,6,7,8-tetrahydro-4H-thieno[2,3-d]azepine (Scheme 1b)

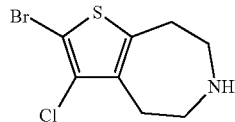

a.) 2-Bromo-3-chloro-4,5,7,8-tetrahydro-thieno[2,3-d]azepine-6-carboxylic acid tert-butyl ester The product of Example 1, step f) (54 mg, 0.21 mmol) was dissolved in CHCl$_3$ (1 ml) and HOAc (1 mL) and treated with hydroquinone (2 mg, 0.02 mmol) and N-bromosuccinimide (38 mg, 0.21 mmol). After stirring at ambient temperature for 20 minutes, N-chlorosuccinimide (28 mg, 0.21 mmol) was added and stirring was continued at ambient temperature for 48 hours. The reaction mixture was poured into saturated sodium bicarbonate (10 ml) and extracted with chloroform (3×5 ml). The combined organic phases were washed with brine (10 ml), dried (MgSO$_4$) and concentrated providing a crude oil, which was used without further purification.

b.) 2-Bromo-3-chloro-5,6,7,8-tetrahydro-4H-thieno[2,3-d]azepine Hydrochloride

The title compound was prepared by the method of Example 1 step h), using the product of step a). $^1$H NMR (300 MHz, DMSO) δ 9.12 (bs, 2H); 3.22-3.31 (m, 4H); 3.13-3.20 (m, 2H); 2.98-3.05 (m, 2H). MS: ESI (positive): 266, 268 (M+H).

EXAMPLE 6

2-(4-Trifluoromethoxy-phenyl)-5,6,7,8-tetrahydro-4H-thieno[2,3-d]azepine (Scheme 2)

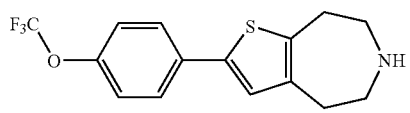

a.) 2-(4-Trifluoromethoxy-phenyl)-4,5,7,8-tetrahydro-thieno[2,3-d]azepine-6-carboxylic acid tert-butyl ester The product of Example 1, step g) (20 mg, 0.06 mmol) was dissolved in DME (5 mL) and treated with palladium acetate (1 mg, 0.004 mmol), triphenylphosphine (4.7 mg, 0.018 mmol) and 1 M sodium carbonate (Na$_2$CO$_3$; 0.45 mL). The mixture was stirred at ambient temperature for 5 minutes and then treated with 4-trifluoromethoxy phenylboronic acid (28.4 mg, 0.138 mmol). After heating for 5 hours at 85° C., additional 4-trifluoromethoxy phenyl-boronic acid (6.2 mg, 0.03 mmol) was added and stirring continued for 12 hours. The reaction mixture was cooled to ambient temperature, passed through a pad of dry celite and filtered through a silica plug eluting with DCM (5 ml) and EtOAc (5 mL). The filtrate was evaporated to give the subtitle compound as a crude oil, which was used without further purification.

b.) 2-(4-Trifluoromethoxy-phenyl)-5,6,7,8-tetrahydro-4H-thieno[2,3-d]azepine

The title compound was prepared by the method of Example 1 step h), using the product of step a). The reaction mixture was concentrated in vacuo and purified by preparative HPLC to give the title compound. $^1$H NMR (300 MHz, DMSO) δ 7.76 (d, J=8 Hz, 2H), 7.48 (d, J=8 Hz, 2H), 7.36 (s, 1H), 2.77-3.06 (m, 8H), 2.0 (s, 1H). ). MS: ESI (positive): 314 (M+H).

EXAMPLE 7

2-(2-Trifluoromethyl-phenyl)-5,6,7,8-tetrahydro-4H-thieno[2,3-d]azepine (Scheme 2)

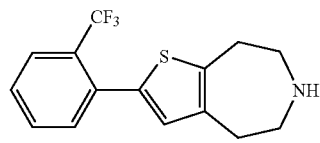

a.) 2-(2-Trifluoromethyl-phenyl)-4,5,7,8-tetrahydro-thieno[2,3-d]azepine-6-carboxylic acid tert-butyl ester The subtitle compound was prepared by the method of Example 6 step a), using 2-trifluoromethyl-phenyl boronic acid.

b.) 2-(2-Trifluoromethyl-phenyl)-5,6,7,8-tetrahydro-4H-thieno [2,3-d]azepine

The title compound was prepared by the method of Example 1 step h), using the product of step a). The reaction mixture was concentrated in vacuo and purified by preparative HPLC to give the title compound. MS: ESI (positive): 298 (M+H).

EXAMPLE 8

2-(4-Fluoro-phenyl)-5,6,7,8-tetrahydro-4H-thieno[2,3-d]azepine (Scheme 2)

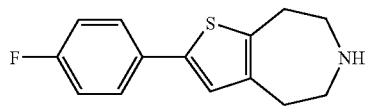

a.) 2-(4-Fluoro-phenyl)-4,5,7,8-tetrahydro-thieno[2,3-d]azepine-6-carboxylic acid tert-butyl ester The subtitle compound was prepared by the method of Example 6 step a), using 4-fluorophenyl boronic acid.

b.) 2-(4-Fluoro-phenyl)-5,6,7,8-tetrahydro-4H-thieno[2,3-d]azepine

The title compound was prepared by the method of Example 1 step h), using the product of step a). The reaction mixture was concentrated in vacuo and purified by preparative HPLC to give the title compound. MS: ESI (positive): 248 (M+H).

EXAMPLE 9

2-(3-Chloro-4-fluoro-phenyl)-5,6,7,8-tetrahydro-4H-thieno[2,3-d]azepine (Scheme 2)

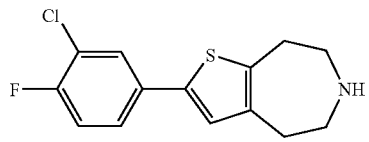

a.) 2-(3-Chloro-4-fluoro-phenyl)-4,5,7,8-tetrahydro-thieno[2,3-d]azepine-6-carboxylic acid tert-butyl ester The subtitle compound was prepared by the method of Example 6 step a), using 3-chloro-4-fluorophenyl boronic acid.

b.) 2-(3-Chloro-4-fluoro-phenyl)-5,6,7,8-tetrahydro-4H-thieno[2,3-d]azepine

The title compound was prepared by the method of Example 1 step h), using the product of step a). The reaction mixture was concentrated in vacuo and purified by preparative HPLC to give the title compound. MS: ESI (positive): 282 (M+H).

EXAMPLE 10

2-(2,5-Dichloro-phenyl)-5,6,7,8-tetrahydro-4H-thieno[2,3-d]azepine (Scheme 2)

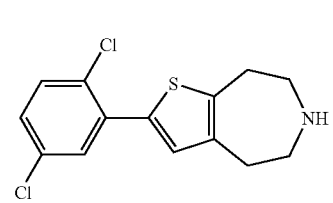

a.) 2-(2.5-dichloro-phenyl)-4,5,7,8-tetrahydro-thieno[2,3-d]azepine-6-carboxylic acid tert-butyl ester The subtitle compound was prepared by the method of Example 6 step a), using 2,4-dichlorophenyl boronic acid.

b.) 2-(2,5-Dichloro-phenyl)-5,6,7,8-tetrahydro-4H-thieno[2,3-d]azepine

The title compound was prepared by the method of Example 1 step h), using the product of step a). The reaction mixture was concentrated in vacuo and purified by preparative HPLC to give the title compound. MS: ESI (positive): 298 (M+H).

EXAMPLE 11

2-(4-Ethyl-phenyl)-5,6,7,8-tetrahydro-4H-thieno[2,3-d]azepine (Scheme 2)

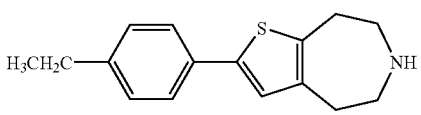

a.) 2-(4-Ethyl-phenyl)-4,5,7,8-tetrahydro-thieno[2,3-d]azepine-6-carboxylic acid tert-butyl ester The subtitle compound was prepared by the method of Example 6 step a), using 4-ethylphenyl boronic acid.

b.) 2-(4-Ethyl-phenyl)-5,6,7,8-tetrahydro-4H-thieno[2,3-d]azepine

The title compound was prepared by the method of Example 1 step h), using the product of step a) except the reaction mixture was concentrated in vacuo and purified by preparative HPLC to give the title compound. MS: ESI (positive): 258 (M+H).

EXAMPLE 12

2-(3-Methoxy-phenyl)-5,6,7,8-tetrahydro-4H-thieno[2,3-d]azepine (Scheme 2)

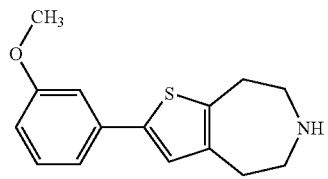

a.) 2-(3-Methoxy-phenyl)-4,5,7,8-tetrahydro-thieno[2,3-d]azepine-6-carboxylic acid tert-butyl ester The subtitle compound was prepared by the method of Example 6 step a), using 3-methoxyphenyl boronic acid.

b.) 2-(3-Methoxy-phenyl)-5,6,7,8-tetrahydro-4H-thieno[2,3-d]azepine

The title compound was prepared by the method of Example 1 step h), using the product of step a) except the reaction mixture was concentrated in vacuo and purified by preparative HPLC to give the title compound. MS: ESI (positive): 260 (M+H).

EXAMPLE 13

2-Phenyl-5,6,7,8-tetrahydro-4H-thieno[2,3-d]azepine (Scheme 2)

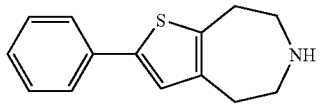

a.) 2-Phenyl-5,6,7,8-tetrahydro-4H-thieno[2,3-d]azepine-6-carboxylic acid tert-butyl ester The subtitle compound was prepared by the method of Example 6 step a), using phenyl boronic acid.

b.) 2-Phenyl-5,6,7,8-tetrahydro-4H-thieno[2,3-d]azepine

The title compound was prepared by the method of Example 1 step h), using the product of step a) except the reaction mixture was concentrated in vacuo and purified by preparative HPLC to give the title compound. MS: ESI (positive): 230 (M+H).

EXAMPLE 14

2-(2-Chloro-6-fluoro-benzyl)-5,6,7,8-tetrahydro-4H-thieno[2,3-d]azepine (Scheme 3)

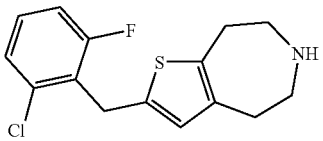

a.) 2-Bromo-4,5,7,8-tetrahydro-thieno[2,3-d]azepine-6-carboxylic acid ethyl ester The product of Example 1, step d) (300 mg, 1.33 mmol) was dissolved in chloroform (3 ml) and acetic acid (3 ml) and treated with N-bromosuccinimide (248 mg, 1.40 mmol) and stirred at ambient temperature for 30 minutes. The reaction mixture was carefully quenched by dilution with saturated sodium bicarbonate (20 ml) and extracted with chloroform (3×20 ml). The combined organic phases were washed with brine (50 ml), dried (MgSO$_4$), and evaporated in vacuo to give a crude oil. Purification by preparative TLC (hexane/ethyl acetate) provided the subtitle compound as an oil. MS: ESI (negative): 302 (M−H).

b.) 2-(2-Chloro-6-fluoro-benzyl)-4,5,7,8-tetrahydro-thieno[2,3-d]azepine-6-carboxylic acid ethyl ester The product of step a) (144 mg, 0.48 mmol) in 2 ml dry diethyl ether was treated with NiCl$_2$ (dppp) (3-5 mol %) followed by dropwise addition of 2-chloro-6-fluorobenzyl magnesiumbromide (0.25 M solution, 1.2 mmol, 4.8 ml) over 30 minutes at ambient temperature. The reaction mixture was heated to reflux for 12 hours. The reaction mixture was cooled to ambient temperature, quenched with 1M HCl (10 ml) and extracted with diethyl ether (3×10 ml). The combined ether extracts were washed with water (30 ml), dried (MgSO$_4$), and evaporated providing a crude oil. Purification by HPLC provided the subtitle compound. MS calculated for C$_{18}$H$_{19}$ClFNO$_2$S+H 369, observed 369.

c.) 2-(2-Chloro-6-fluoro-benzyl)-5,6,7,8-tetrahydro-4H-thieno[2,3-d]azepine

The title compound was prepared by the method of Example 3 step b), using the product of step b). $^1$H NMR (300 MHz, C$_6$D$_6$) δ 6.94 (d, J=8 Hz, 1H), 6.52-6.70 (m, 2H), 6.49 (s, 1H), 4.17 (s, 2H), 2.47-2.78 (m, 8H), 2.03 (s, 1H). MS: ESI (positive): 296 (M+H).

EXAMPLE 15

3-Bromo-2-(2-chloro-6-fluoro-benzyl)-5,6,7,8-tetrahydro-4H-thieno[2,3-d]azepine (Scheme 3)

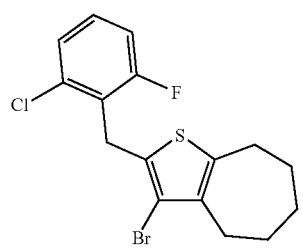

a.) 3-Bromo-2-(2-chloro-6-fluoro-benzyl)-4,5,7,8-tetrahydro-thieno[2,3-d]azepine-6-carboxylic acid ethyl ester The product of Example 14, step b) (49 mg, 0.13 mmol) was dissolved in a 1:1 mixture of CHCl$_3$/HOAc (1 mL) and treated with sodium acetate (43 mg, 0.52 mmol) and N-bromosuccinimide (27 mg, 0.15 mmol). The reaction mixture was heated at 60° C. and stirred for 30 minutes. The reaction mixture was cooled to ambient temperature, diluted with water (5 ml), and extracted with chloroform (3×5 ml). The combined organic extracts were washed with 10% KOH, dried (MgSO$_4$), and evaporated in vacuo to give the subtitle compound as an oil, which was used without further purification.

b.) 3-Bromo-2-(2-chloro-6-fluoro-benzyl)-5,6,7,8-tetrahydro-4H-thieno[2,3-d]azepine The title compound was prepared by the method of Example 3 step b), using the product of step a). $^1$H NMR (300 MHz, $C_6D_6$) δ 6.33-6.78 (m, 3H), 4.09 (s, 2H), 2.18-3.20 (m, 8H), 1.62 (s, 1H). MS calculated for $C_{15}H_{14}BrClFNS+H$ 374, observed 374.

EXAMPLE 16

2-Bromo-3-methyl-5,6,7,8-tetrahydro-4H-thieno[2,3-d]azepine (Scheme 4)

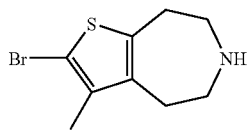

a.) (5-Bromo-4-methyl-thiophen-2-yl)-hydroxy-acetic acid ethyl ester

2-Bromo-3-methyl thiophene (13.2 mL, 113 mmol) was stirred in 1 liter of DCM at 0° C. Ethylchloro oxalate (13.9 mL, 124 mmol) was added followed by $AlCl_3$ (16.5 g, 124 mmol). After stirring for 10 minutes, the reaction was carefully poured over ice (~500 mL) and EtOH (~300 mL). Upon warming to room temperature, the product was extracted into DCM (2×) and dried over $MgSO_4$. Concentration gave 37.5 g of an orange solid which was dissolved in THF (1 liter) and treated with $NaBH(OAc)_3$ (36 g, 170 mmol). After heating to 60° C. for 1 hour, the reaction was cooled and quenched with HOAc (13.6 mL, 226 mmol). The reaction was concentrated and the residue was partitioned between DCM/EtOH (5:1) and water. The aqueous layer was extracted 1× with DCM and the combined organic extracts were dried over $MgSO_4$ and concentrated to give the subtitle compound (35 g), which was used without further purification.

b.) (5-Bromo-3-ethoxycarbonylmethyl-4-methyl-thiophen-2-yl)-acetic acid ethyl ester The product of step a) (—113 mmol) was treated with 300 mL decalin, 103 mL of triethylorthoacetate (565 mmol), and hexanoic acid (6.2 mL, 50 mmol). The reaction was heated to 180° C. for 10 minutes after which time another 50 mmol of hexanoic acid was added. After heating 10 minutes, additional hexanoic acid was added (50 mmol) and the reaction was again heated for 10 minutes. The reaction was cooled and concentrated under vacuum with heat to give the sub-title compound as an oil that was used without further purification.

c.) 2-[5-Bromo-3-(2-hydroxy-ethyl)-4-methyl-thiophen-2-yl]-ethanol

The product of step b) (~113 mmol) was dissolved in EtOH (1 liter) and cooled to 0° C. then treated with 170 mL of 2 M NaOH. After stirring for 24 hours, the resulting precipitate was filtered and washed with ethanol to give 15 g of the disodium salt. A portion of this material (3 g, 8.9 mmol) was dissolved in 90 mL THF and treated with 4M HCl in dioxane (4 mL, 16 mmol). After stirring vigorously for ½ hour, $BH_3$-THF (44.4 mL of 1 M) was added and the solution was stirred at room temperature for 2 hours. The reaction was quenched cautiously with saturated $NaHCO_3$ and concentrated. The crude residue was partitioned between EtOAc and water (150 mL each). The organic layer was dried over $MgSO_4$ and concentrated to give 1.94 g of the sub-title compound.

d.) 6-Benzyl-2-bromo-3-methyl-5,6,7,8-tetrahydro-4H-thieno[2,3-d]azepine

The product of step c) (1.94 g, 7.3 mmol) was dissolved in 75 mL of DCM, cooled to 0° C. and treated with $Et_3$ N (29.3 mmol, 4.1 mL) followed by MsCl (22 mmol, 1.71 mL). After 1 hour, additional $Et_3$ N and MsCl were added (2 eq and 1.5 eq, respectively) and the reaction was stirred an additional hour. The crude reaction was poured over 5% citric acid, extracted into DCM, and washed with saturated $NaHCO_3$. After drying the organic solution over $MgSO_4$ and concentration, the crude product was dissolved in dioxane (200 mL) and treated with $K_2CO_3$ (36.6 mmol, 5.0 g). After heating to reflux, $BnNH_2$ (22 mmol, 2.4 mL) was added and the reaction was refluxed overnight. The reaction was cooled, filtered, and concentrated. The sub-title compound was purified by silica gel chromatography (10% EtOAc in hexanes) to give 419 mg of the subtitle compound.

e.) 2-Bromo-3-methyl-5,6,7,8-tetrahydro-4H-thieno[2,3-d]azepine

The product of step d) (80 mg, 0.24 mmol) was dissolved in 2 mL DCE. 2-Chloroethyl chloroformate (103 uL, 0.95 mmol) was added and the reaction was stirred at room temperature for 15 minutes. The reaction was quenched with 3 mL MeOH and the crude mixture was briefly heated to reflux and then concentrated to dryness. The crude residue was dissolved in ½ mL of MeOH and triturated with ether to give 47 mg of the title compound as a white solid. $^1$H NMR ($CD_3OD$) δ 3.36-3.30 (m, 4H), 3.12 (t, J=5.2 Hz, 2H), 3.00 (t, J=5.1 Hz, 2H), 2.11 (s, 3H); MS: ESI (positive): 246,248 (M+H).

EXAMPLE 17

3-Methoxy-2-methyl-5,6,7,8-tetrahydro-4H-thieno[2,3-d]azepine (Scheme 5)

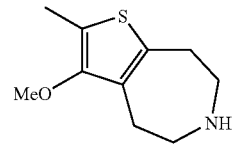

a.) 5-Oxo-azepane-1,4-dicarboxylic acid diethyl ester

4-Oxo-piperidine-1-carboxylic acid ethyl ester (20 g, 117 mmol) was dissolved in 120 mL $Et_2O$ and cooled to −30° C. $BF_3$-$OEt_2$ (14.8 mL) and ethyl diazoacetate (16 mL, 152 mmol) were added simultaneously (each in 15 mL $Et_2O$) over the course of 30 minutes, maintaining an internal temperature of approximately −20° C. The reaction was warmed to room temperature and stirred for 3 hours after which time the reaction was quenched carefully with 30% $K_2CO_3$ (60 mL). The organic layer was dried over $K_2CO_3$ and concentrated to give 30.4 g of the subtitle compound.

b.) 3-Hydroxy-4,5,7,8-tetrahydro-thieno[2,3-d]azepine-2,6-dicarboxylic acid diethyl ester The product of step a) (20 g, 77.8 mmol) was dissolved in 300 mL EtOH. The solution was cooled to 0° C. and HCl gas was bubbled into the reaction for 10 minutes. Ethyl thioglycolate (7.8 mL, 77.8 mmol) was added and HCl gas was again bubbled into the solution for 3 minutes. After stirring for 4 days at room temperature, the reaction was concentrated, neutralized with saturated NaHCO$_3$, and extracted into ether (200 mL). After drying the extracts over MgSO$_4$ and concentration, the residue was dissolved in EtOH (100 mL) and treated with NaOEt (100 mL of 21% NaOEt in EtOH). After stirring overnight, the reaction was diluted with 500 mL water and washed with 300 mL DCM. The DCM was extracted with 150 mL water and then repeatedly extracted with 5% KOH (~10×75 mL). The combined aqueous extracts were acidified with concentrated HCl and extracted into DCM (4×200 mL). The DCM extracts were dried over MgSO$_4$ and concentrated to give 7.5 g of the subtitle compound as an oil.

c.) 3-Methoxy-4,5,7,8-tetrahydro-thieno[2,3-d]azepine-2,6-dicarboxylic acid diethyl ester The product of step b) (2.3 g, 7.3 mmol) was dissolved in 60 mL of 1:1 MeOH:THF. Diisopropylethylamine (1.9 mL, 10.9 mmol) was added followed by TMSCHN$_2$ (10.9 mL of 2M). The reaction was stirred overnight at room temperature then quenched carefully with 0.4 ML HOAc. After stirring ½ hour, the reaction was partitioned between DCM and 1M HCl (100 mL each). The organic layer was dried over MgSO$_4$ and concentrated to give 2.75 g of the subtitle compound.

d.) 2-Hydroxymethyl-3-methoxy-4,5,7,8-tetrahydro-thieno[2,3-d]azepine-6-carboxylic acid ethyl ester The product of step c) (2.5 g, 7.8 mmol) was dissolved in 125 mL dry THF and treated with LiCl (0.65 g, 15.3 mmol) followed by LiBH$_4$ (15.3 mL of 2M). After stirring for 1 hour, the reaction was quenched carefully with EtOH and HOAc till no gas evolution was observed. The crude reaction mixture was partitioned between water and DCM. The organic extract was dried over MgSO$_4$ and concentrated to give 2.3 g of a clear oil which was purified by silica chromatography (30% EtOAc/Hex) to give 1.03 g of the subtitle compound.

e.) 3-Methoxy-2-methyl-5,6,7,8-tetrahydro-4H-thieno[2,3-d]azepine

The product of step d) (70 mg, 0.25 mmol) was dissolved in 10 mL EtOAc and treated with 35 mg of 10% Pd/C (wet, Degussa type E101) and stirred rapidly under an atmosphere of H$_2$ for 3 hour. The reaction was filtered and concentrated. The crude residue was dissolved in 1 mL EtOH and treated with 1 mL 40% aqueous KOH. After heating to 80° C. overnight, the reaction was diluted with water and the product was extracted 2× into DCM. The title compound was obtained upon purification by preparative HPLC-MS. $^1$H NMR (CDCl$_3$) δ 3.69 (s, 3H), 3.21-3.14 (m, 4H), 3.00 (t; J=5.2 Hz, 2H), 2.88 (t, J=5.1 Hz, 2H), 2.29 (s, 3H); MS: ESI (positive): 198 (M+H).

EXAMPLE 18

2-Bromo-3-methoxy-5,6,7,8-tetrahydro-4H-thieno[2,3-d]azepine (Scheme 5)

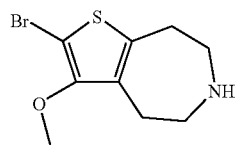

a.) 3-Methoxy-4,5,7,8-tetrahydro-thieno[2,3-d]azepine-2,6-dicarboxylic acid 6-ethyl ester The product from Example 17, step c) (1.0 g, 3.19 mmol) was stirred in ethanol (20 mL) with 1M NaOH (6.38 mL, 6.38 mmol) at 80° C. overnight. The reaction was cooled to ambient temperature, acidified with a 10% HCl solution, and extracted with 5% EtOH in DCM (×2). The organic extracts were combined and washed with water. The organic layer was dried over NaSO$_4$, filtered, and concentrated to give 912 mg of the subtitled compound that was used without further purification. MS: ESI (positive): 300 (M+H).

b.) 2-tert-Butoxycarbonylamino-3-methoxy-4,5,7,8-tetrahydro-thieno[2,3-d]azepine-6-carboxylic acid ethyl ester A solution of the product from step a) (790 mg, 3.01 mmol) was stirred with diphenylphosphoryl azide (647 µL, 3.01 mmol) and triethylamine (418 µL, 3.01 mmol) in tert-butanol (20 mL) at 80° C. overnight. The reaction was cooled to room temperature and poured into a saturated aqueous solution of NaHCO$_3$. The resultant mixture was extracted with ethyl acetate. The organic extract was dried over MgSO$_4$ and purified by silica gel chromatography (EtOAc/Hex-gradient) to give 852 mg of the subtitle compound. MS: ESI (positive): 370 (M+H).

c.) 3-Methoxy-4,5,7,8-tetrahydro-thieno[2,3-d]azepine-6-carboxylic acid ethyl ester The product from step b) (256 mg, 0.69 mmol) was stirred in TFA (2 mL) for 30 minutes. The reaction was concentrated and dissolved in EtOH (5 mL). Isoamyl nitrite (140 µL, 1.04 mmol) and Cu(OAc)$_2$ (188 mg, 1.04 mmol) were added to the solution and the reaction was stirred at room temperature overnight. The reaction was filtered through a silica plug and purified by silica gel chromatography (EtOAc/Hex-gradient) to give 17 mg of the subtitle compound. MS: ESI (positive): 271 (M+H).

d.) 2-Bromo-3-methoxy-4,5,7,8-tetrahydro-thieno[2,3-d]azepine-6-carboxylic acid ethyl ester The product of step c) (17 mg, 0.067 mmol) was dissolved in 1 mL 1:1 acetic acid:CHCl$_3$ and treated with N-bromosuccinimide (12 mg, 0.068 mmol). After 30. minutes, the reaction solution was added dropwise to a solution of saturated sodium bicarbonate and extracted with ethyl acetate. The organic extracts were concentrated to give the subtitle compound, which was used without further purification.

e.) 2-Bromo-3-methoxy-5,6,7,8-tetrahydro-4H-thieno[2,3-d]azepine

A 40% KOH solution in water (1 mL) was added to the product of step-d) (~0.067 mmol) in 1 mL ethanol. After heating to 80° C. overnight, the reaction mixture was cooled to ambient temperature and partitioned between water and DCM. The organic extract was concentrated and purified by preparative LCMS to give the title compound. $^1$H NMR (CD$_3$OD) δ 3.83 (s, 3H), 3.22-3.28 (m, 4H), 3.05 (t, J=5.1 Hz, 2H), 2.93 (t, J=5.1 Hz, 2H); MS: ESI (positive): 262 (M+H).

EXAMPLE 19

2-Chloro-3-methoxy-5,6,7,8-tetrahydro-4H-thieno[2,3-d]azepine (Scheme 5)

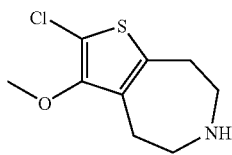

a.) 2-Chloro-3-methoxy-4,5,7,8-tetrahydro-thieno[2,3-d]azepine-6-carboxylic acid ethyl ester The sub-title compound was prepared by the method of Example 18, step d) using the product from Example 18, step c) and N-chlorosuccinimide.

b.) 2-Chloro-3-methoxy-5,6,7 8-tetrahydro-4H-thieno[2,3-d]azepine

The title compound was prepared by the method described in Example 18, step e) using the product from step a). $^1$H NMR (CD$_3$OD) δ 3.86 (s, 3H), 3.19-3.26 (m, 4H), 3.01 (t, J=5.4 Hz, 2H), 2.88 (t, J=5.4 Hz, 2H). MS: ESI (positive): 218 (M+H).

EXAMPLE 20

2-Isopropenyl-3-methoxy-5,6,7,8-tetrahydro-4H-thieno[2,3-d]azepine (Scheme 5)

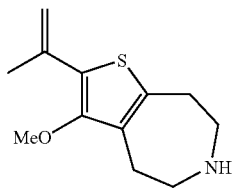

a.) 2-Isopropenyl-3-methoxy-4,5,7,8-tetrahydro-thieno[2,3-d]azepine-6-carboxylic acid ethyl ester The product of Example 17, step c) (59 mg, 0.19 mmol) was dissolved in 5 mL THF and cooled to 0° C. MeMgBr (0.54 mL of 1.4 M) was added and the reaction was stirred at room temperature for 1 hour. The reaction was quenched with water and HOAc (~3 mL of 10:1) and extracted into DCM (2×5 mL). The organic extracts were concentrated to give the sub-title compound as an oil, which was used without further purification.

b.) 2-Isopropenyl-3-methoxy-5,6,7,8-tetrahydro-4H-thieno[2,3-d]azepine

The product of step a) (~0.19 mmol) was treated with 2 mL each of EtOH and 40% aqueous KOH. After heating to 100° C. for 16 hours, the reaction was diluted with water and the product was extracted into DCM (2×4 mL). The organic extracts were concentrated and the title compound was purified by preparative HPLC-MS. $^1$H NMR (CD$_3$OD) δ 5.41 (s, 1H), 5.02 (t, J=1.6 Hz, 1H), 3.14-3.08 (m, 4H), 2.96 (t, J=5.1 Hz, 2H), 2.82 (t, J=5.1 Hz, 2H), 2.09 (s, 3H); MS: ESI (positive): 224 (M+H).

EXAMPLE 21

2-tert-Butyl-3-methyl-5,6,7,8-tetrahydro-4H-thieno[2,3-d]azepine (Scheme 9)

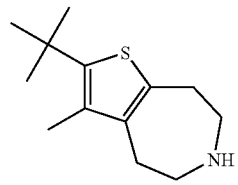

a.) 3-Methyl-4,5,7,8-tetrahydro-thieno[2,3-d]azepine-6-carboxylic acid ethyl ester The product of Example 16, step e) (475 mg, 1.68 mmol) was dissolved in 50 mL DCM and treated with Et$_3$N (585 uL, 4.2 mmol) and ethyl chloroformate (210 uL, 2.18 mmol). After stirring for 3 days at room temperature, the reaction was concentrated onto silica gel and purified by silica gel chromatography (EtOAc/Hex-gradient) to give 380 mg of the ethyl carbamate. The ethyl carbamate (60 mg, 0.19 mmol) was dissolved in 4 mL EtOH and treated with ~10 mg of 10% Pd/C (wet, Degussa grade E101) and stirred under an atmosphere of hydrogen for 12 hours. Filtration and concentration gave the sub-title compound.

b.) 2-tert-Butyl-3-methyl-4,5,7,8-tetrahydro-thieno[2,3-d]azepine-6-carboxylic acid ethyl ester The product of step a) (37 mg, 0.16 mmol) was stirred in 1.5 mL DCE. t-Butanol (19 uL, 0.20 mmol) was added followed by BF$_3$-OEt$_2$ (20 uL, 0.16 mmol). The reaction was heated to 60° C. for 1 hour. Concentration gave the subtitle compound, which was used without further purification.

c.) 2-tert-Butyl-3-methyl-5,6,7,8-tetrahydro-4H-thieno[2,3-d]azepine

The product of step b) was treated with 2 mL each of EtOH and 40% aqueous KOH. After heating to 100° C. for 12 hours, the reaction was cooled, diluted with water, and extracted 2× into DCM. The title product was purified by preparative HPLC-MS. MS: ESI (positive): 224 (M+H).

EXAMPLE 22

2-Isopropyl-3-methoxy-5,6,7,8-tetrahydro-4H-thieno[2,3-d]azepine (Scheme 5)

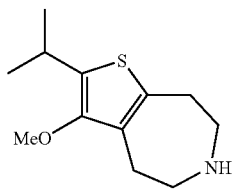

a.) 2-Isopropyl-3-methoxy-4,5,7,8-tetrahydro-thieno[2,3-d]azepine-6-carboxylic acid ethyl ester The product of Example 20, step a) (35 mg, 0.13 mmol) was dissolved in 2 mL of EtOH and treated with 50 mg of 10% Pd/C (wet, Degussa grade E101). After stirring 3 hours at room temperature under an atmosphere of hydrogen, the reaction was filtered and concentrated to give the subtitle compound as an oil.

b.) 2-Isopropyl-3-methoxy-5,6,7,8-tetrahydro-4H-thieno[2,3-d]azepine

The product of step a) was deprotected according to the procedure described for Example 20, step b). Purification by preparative HPLC-MS gave the title compound. $^1$H NMR (CD$_3$OD) δ 3.69 (s, 3H), 3.29-3.21 (m, 5H), 3.03 (t, J=5.2 Hz, 2H), 2.88 (t, J=5.4 Hz, 2H), 1.24 (d, J=6.9 Hz, 6H); MS: ESI (positive): 226 (M+H).

EXAMPLE 23

2-Bromo-4-methyl-5,6,7,8-tetrahydro-4H-thieno[2,3-d]azepine (Scheme 6)

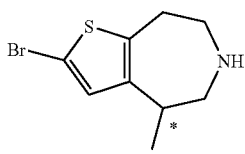

a.) 4-Methylene-4,5 7,8-tetrahydro-thieno[2,3-d]azepine-6-carboxylic acid ethyl ester Methyl triphenylphosphonium bromide (6.3 g, 17.6 mmol) was dissolved in 150 mL THF and cooled to 0° C. KHMDS (3.2 g, 16.2 mmol) was added portionwise and the reaction was stirred for ½ hour. The product of Example 1, step c) (3.0 g, 12.5 mmol) was added as a solution in 25 mL THF. The reaction was warmed to room temperature and stirred for 1 hour. The mixture was concentrated and the title product was purified by silica gel chromatography (EtOAc/Hexanes-gradient) to give 2.6 g of the subtitle compound.

b.) 4-Methyl-4,5,7,8-tetrahydro-thieno[2,3-d]azepine-6-carboxylic acid ethyl ester The product of step a) (2.6 g, 10.8 mmol) was dissolved in 100 mL EtOH and treated with 0.5 g of 10% Pd/C (wet, Degussa type E101). After stirring rapidly for 14 hours under an atmosphere of hydrogen, the reaction was filtered through celite and concentrated to give 2.3 g of the subtitle compound as a clear oil. MS: ESI (positive): 240 (M+H).

c.) 2,3-Dibromo-4-methyl-4,5,7,8-tetrahydro-thieno[2,3-d]azepine-6-carboxylic acid ethyl ester The product of step b) (5.6 g, 23.4 mmol) was dissolved in 250 mL cyclohexane and treated with NaHCO$_3$ (11.8 g, 140 mmol). Bromine (3.6 mL, 70.3 mmol) was added slowly and the reaction was stirred for ½ hour at room temperature after which time it was quenched with Na$_2$SO$_3$ (180 mL of 5% aqueous). After stirring rapidly for 15 minutes, EtOAc was added (~100 mL) and the organic layer was removed and dried over MgSO$_4$ to give 9.1 g of the sub-title compound. The racemic material was separated using a Chiralpakg AD-RH(V 20×250 mm column from Chiral Technologies (10 mL/min MeOH mobile phase) to give enantiomer 1 (rt=9.8 minutes) and enantiomer 2 (rt=11.4 minutes) of the subtitle compound.

d.) 4-Methyl-4,5,7,8-tetrahydro-thieno[2,3-d]azepine-6-carboxylic acid ethyl ester The product of step c) (800 mg, 2.0 mmol) was dissolved in 150 mL EtOH and treated with 800 mg of 10% Pd/C (wet, Degussa grade E101). After stirring overnight, another 300 mg of Pd was added and stirring was continued 3 hours. The reaction was filtered through celite, diluted with DCM (300 mL), and washed with water (1×300 mL). The organic layer was dried over MgSO$_4$ and concentrated to give 475 mg of the subtitle compound.

e.) 2-Bromo-4-methyl-4,5,7,8-tetrahydro-thieno[2,3-d]azepine-6-carboxylic acid ethyl ester The product of step d) (80 mg, 0.35 mmol) was dissolved in 2 mL of 1:1 CHCl$_3$/HOAc. N-Bromo-succinimide (62 mg, 0.35 mmol) was added and the reaction was stirred for 15 minutes. Concentration and purification by silica gel chromatography gave the subtitle compound as a yellow oil.

f.) 2-Bromo-4-methyl-5,6,7,8-tetrahydro-4H-thieno[2,3-d]azepine

The product of step e) was deprotected according to the procedure described for Example 20, step b) to provide the title compound. $^1$H NMR (CD$_3$OD) δ 6.97 (s, 1H), 3.46-3.11 (m, 7H), 1.39 (d, J=7.2 Hz, 3H); MS: ESI (positive): 246,248 (M+H).

EXAMPLE 24

2-Bromo-8-methyl-5,6,7,8-tetrahydro-4H-thieno[2,3-d]azepine (Scheme 7)

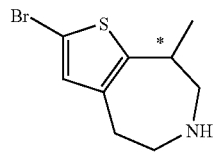

a.) 2-Thiophen-3-yl-ethylamine

Thiophen-3-yl-acetonitrile (5.0 g, 40.6 mmol) was dissolved in 50 mL THF. $BH_3$-THF (61 mL, 1M in THF) was added slowly. The reaction was heated to 60° C. overnight then quenched carefully with 4% aqueous HCl until no effervescence was observed. The crude reaction mixture was then partitioned between EtOAc and water (300 mL each). The aqueous layer was acidified with 30% NaOH to pH ~12 and the product was extracted into DCM/EtOH (4:1, 3×). The organic extracts were dried over $MgSO_4$ and concentrated to give 2.9 g of the subtitle compound as an oil.

b.) [Ethoxycarbonyl-(2-thiophen-3-yl-ethyl)-amino]-acetic acid ethyl ester

The subtitle compound was prepared from the product of step a) using the procedure described in Example 1, step a).

c.) [Ethoxycarbonyl-(2-thiophen-3-yl-ethyl)-amino]-acetic acid

The subtitle compound was prepared from the product of step b) using the procedure described for Example 1, step b).

d.) 8-Oxo-4,5,7,8-tetrahydro-thieno[2,3-d]azepine-6-carboxylic acid ethyl ester The subtitle compound was prepared from the product of step c) using the procedure described for Example 1, step c).

e.) 8-Methylene-4,5,7,8-tetrahydro-thieno[2,3-d]azepine-6-carboxylic acid ethyl ester $MePPh_3$ Br (785 mg, 2.2 mmol) was dissolved in 7 mL THF and treated with KHMDS (408 mg, 2.04 mmol). After stirring for 30 minutes, the product of step d) (350 mg, 1.5 mmol) was added as a solution in 3 mL THF. After stirring for 1 hour, the reaction was diluted with EtOAc and washed with water. The organic layer was concentrated and the product was purified by silica gel chromatography (EtOAc/Hex-gradient) to give 188 mg of the subtitle compound.

f.) 8-Methyl-4,5,7,8-tetrahydro-thieno[2,3-d]azepine-6-carboxylic acid ethyl ester The product of step a) (59 mg, 0.25 mmol) was dissolved in 5 mL EtOH and treated with 75 mg of 10% Pd/C (wet, Degussa grade E101). After stirring for 1 hour under an atmosphere of hydrogen, the reaction was filtered and concentrated to give the subtitle compound that was used without further purification.

g.) 2-Bromo-8-methyl-5,6,7,8-tetrahydro-4H-thieno[2,3-d]azepine

The product of step f) was dissolved in 2 mL of 1:1 $CHCl_3$/HOAc and treated with NBS (62 mg, 0.35 mmol). After stirring for 10 minutes, the reaction was concentrated to dryness and filtered through a pad of silica gel, eluting with EtOAc. The eluent was concentrated and the residue was treated with 2 mL each EtOH and 40% aqueous KOH. After heating for 14 hours at 100° C., the reaction was diluted with water and extracted 2× into DCM. The title compound was purified by preparative HPLC-MS. The two enantiomers were separated using a Chiralpak® AD-RH® 20×250 mm column from Chiral Technologies (10 mL/min MeOH mobile phase) to give enantiomer 1 (rt=11.6 minutes) and enantiomer 2 (rt=13.6 minutes) of the title compound. $^1$H NMR ($CD_3OD$) δ 6.92 (s, 1H), 3.48-3.34 (m, 3H), 3.17-2.99 (m, 4H), 1.44 (d, J=7.2 Hz, 3H); MS: ESI (positive): 246, 248 (M+H).

EXAMPLE 25

2-Bromo-8-spirocyclopropyl-5,6,7,8-tetrahydro-4H-thieno[2,3-d]azepine (Scheme 7)

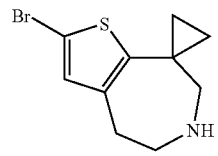

a.) 8-Spirocyclopropyl-4,5,7,8-tetrahydro-thieno[2,3-d]azepine-6-carboxylic acid ethyl ester A solution of $ZnCl_2$ (2.49 mL, 1M in hexane) and $CH_2I_2$ (100 μL, 1.24 mmol) were stirred at 0° C. in DCM for 30 minutes. The product from Example 24, step e) (59 mg, 0.25 mmol) was added as a solution in DCM (1 mL) and the reaction was stirred at ambient temperature for 48 hours. The reaction was diluted with water and extracted into DCM. The organic layer was washed with saturated $NH_4Cl$, water, and brine. Concentration of the organic layer gave the sub-title compound, which was used without further purification. MS: ESI (positive): 252 (M+H).

b.) 2-Bromo-8-spirocyclopropyl-4,5,7,8-tetrahydro-thieno[2,3-d]azepine-6-carboxylic acid ethyl ester The subtitle compound was prepared by the method described in Example 18, step d) using the product from step a) and was used in crude form without purification. MS: ESI (positive): 330 (M+H).

c.) 2-Bromo-8-spirocyclopropyl-5,6,7,8-tetrahydro-4H-thieno[2,3-d]azepine

The title compound was prepared by the method described in Example 18, step e) using the product from step b). $^1$H NMR ($CD_3OD$) δ 6.84 (s, 1H), 3.20 (t, J=5.1 Hz, 2H), 3.02 (t, J=5.1 Hz, 2H), 3.06 (s, 2H), 1.08 (d, J=9.6 Hz, 2H), 1.05 (d, J=9.6 Hz, 2H). MS: ESI (positive): 258 (M+H).

EXAMPLE 26

2-(Pyrrolidine-1-sulfonyl)-5,6,7,8-tetrahydro-4H-thieno[2,3-d]azepine (Scheme 8)

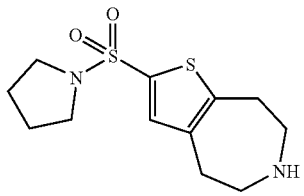

a.) 2-Chlorosulfonyl-4,5,7,8-tetrahydro-thieno[2,3-d]azepine-6-carboxylic acid ethyl ester The product of Example 1, step d) (400 mg, 1.8 mmol) was dissolved in 10 mL CHCl$_3$ and treated with chlorosulfonic acid (355 uL, 1.8 mmol). After 5 minutes, the reaction was quenched over ice and immediately extracted into DCM (2×10 mL). The organic extracts were dried over MgSO$_4$ and concentrated to give 200 mg of the subtitle compound as a solid, which was used without further purification.

b.) 2-(Pyrrolidine-1-sulfonyl)-5,6,7,8-tetrahydro-4H-thieno[2,3-d]azepine

The product of step a) (45 mg, 0.14 mmol) was stirred in 2 mL CHCl$_3$ and treated with pyrrolidine (46 uL, 0.55 mmol). After stirring for 5 minutes, the reaction was concentrated to dryness and the residue was dissolved in 2 mL each of EtOH and 40% aqueous KOH. The reaction was heated in a sealed vessel to 100° C. overnight. Upon cooling, the reaction was diluted with water and the product was extracted into DCM (4×3 mL). The organic extracts were concentrated and the title compound was purified by preparative HPLC-MS. $^1$H NMR (CD$_3$OD) δ 7.42 (s, 1H), 3.43-3.34 (m, 4H), 3.31-3.24 (m, 6H), 3.13 (t, J=5.2 Hz, 2H), 1.81-1.76 (m, 4H); MS: ESI (positive): 287 (M+H).

EXAMPLE 27

5,6,7,8-Tetrahydro-4H-thieno[2,3-d]azepine-2-sulfonic acid dimethylamide (Scheme 8)

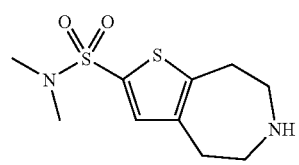

The title compound was prepared according to the procedure outlined in Example 26, step b) using dimethyl amine hydrochloride and Et$_3$N. $^1$H NMR (CD$_3$OD) δ 7.38 (s, 1H), 3.44-3.27 (m, 4H), 3.32-3.26 (m, 2H), 3.17-3.14 (m, 2H), 2.72 (s, 6H); MS: ESI (positive): 261 (M+H).

EXAMPLE 28

3-Methyl-5,6,7,8-tetrahydro-4H-thieno[2,3-d]azepine-2-sulfonic acid dimethylamide (Scheme 8)

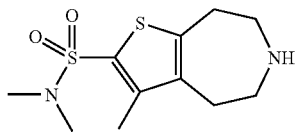

a.) 2-Chlorosulfonyl-3-methyl-4,5,7,8-tetrahydro-thieno[2,3-d]azepine-6-carboxylic acid ethyl ester The subtitled compound was prepared according to the procedure outlined in Example 26, step a) using the intermediate from Example 21, step a). The product was used without further purification.

b.) 3-Methyl-5,6,7,8-tetrahydro-4H-thieno[2,3-d]azepine-2-sulfonic acid dimethylamide The title compound was prepared according to the procedure outlined for Example 26, step b) using the product from step a) and dimethyl amine hydrochloride and Et$_3$N. $^1$H NMR (CD$_3$OD) δ 3.41-3.35 (m, 4H), 3.24 (dd, J=5.1, 6.6 Hz, 2H), 3.04 (t, J=5.2 Hz, 2H), 2.75 (s, 6H), 2.41 (s, 3H); MS: ESI (positive): 275 (M+H).

EXAMPLE 29

5,6,7,8-Tetrahydro-4H-thieno[2,3-d]azepine-2-carboxylic acid cyclopentylamide (Scheme 8)

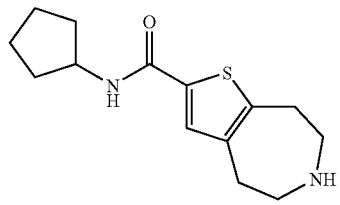

a.) 2-Cyclopentylcarbamoyl-4,5,7,8-tetrahydro-thieno[2,3-d]azepine-6-carboxylic acid ethyl ester The product from Example 1, step d) (50 mg, 0.222 mmol) was stirred with isocyanato-cyclopentane (25 μL, 0.222 mmol) and AlCl$_3$ (35 mg, 0.266 mmol) in dichloroethane (2 mL) at ambient temperature for 4 hours. Additional isocyanato-cyclopentane (25 μL, 0.222 mmol) and AlCl$_3$ (35 mg, 0.266 mmol) were added and the reaction was stirred overnight. The reaction was partitioned between water and DCM. The organic layer was washed with water and concentrated to give the sub-title compound, which was used without further purification. MS: ESI (positive): 337 (M+H).

b.) 5,6,7,8-Tetrahydro-4H-thieno[2,3-d]azepine-2-carboxylic acid cyclopentylamide The product from step b) (37 mg, 0.111 mmol) was treated with TMSI (50 µL, 0.333 mmol) in DCM (2 mL) and stirred at 50° C. overnight. The reaction was then treated with methanol (1 mL), concentrated to dryness, and purified by preparative LC-MS to give the title compound. MS: ESI (positive): 265 (M+H).

EXAMPLE 30

5,6,7,8-Tetrahydro-4H-thieno[2,3-d]azepine-2-carboxylic acid dimethylamide (Scheme 8)

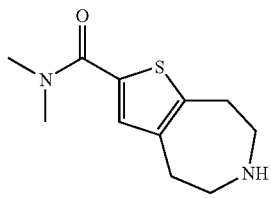

a.) 2-Dimethylcarbamoyl-4,5,7,8-tetrahydro-thieno[2,3-d]azepine-6-carboxylic acid ethyl ester The product from Example 1, step d) (50 mg, 0.22 mmol) was stirred in dichloroethane with phosgene iminium chloride (84 mg, 0.518 mmol) and AlCl₃ (35 mg, 0.266 mmol) at 75° C. overnight. The reaction was cooled to ambient temperature, quenched with water (2 mL) and extracted into DCM. The organic layer was then passed through a pad of celite and concentrated to give the subtitle compound that was used without further purification. MS: ESI (positive): 297 (M+H).

b.) 5,6,7,8-Tetrahydro-4H-thieno[2,3-d]azepine-2-carboxylic acid dimethylamide The title compound was prepared by the method described in Example 29, step b) using the product from step a). MS: ESI (positive): 225 (M+H).

EXAMPLE 31

(R,S)-2-Chloro-8-methyl-5,6,7,8-tetrahydro-4H-thieno[2,3-d]azepine (Scheme 7)

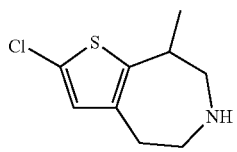

The title compound was prepared from the intermediate described in Example 24, step f) and N-chloro succinimide using the procedure from Example 24, step g). MS: ESI (positive): 202, 204 (M+H).

EXAMPLE 32

2,3-Dibromo-4-methyl-5,6,7,8-tetrahydro-4H-thieno[2,3-d]azepine (Scheme 6)

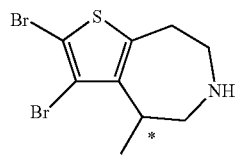

The product of Example 23, step c) was deprotected by the procedure described in Example 20, step b) to provide the title compound. ¹H NMR (CD₃OD) δ 3.60-3.52 (m, 3H), 3.35-3.11 (m, 4H), 1.33 (d, J=6.9 Hz, 3H); MS: ESI (positive): 324, 326, 328 (M+H).

EXAMPLE 33

(R,S)-2-Bromo-4-methoxy-5,6,7,8-tetrahydro-4H-thieno[2,3-d]azepine (Scheme 6)

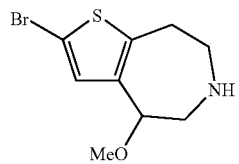

a.) (R,S)-4-Hydroxy-4,5,7,8-tetrahydro-thieno[2,3-d]azepine-6-carboxylic acid ethyl ester Sodium borohydride (154 mg, 4.18 mmol) was added to a solution of the product from Example 1, step c) (200 mg, 0.837 mmol) in ethanol (2 mL) and stirred at ambient temperature for 30 minutes. The reaction was quenched with acetic acid and partitioned between DCM and water. The organic layer was washed with water and concentrated to give the subtitle compound, which was used without further purification. MS: ESI (positive): 264 (M+Na).

b.) (R,S)-4-Methoxy-4,5,7,8-tetrahydro-thieno[2,3-d]azepine-6-carboxylic acid ethyl ester The product from step a) (160 mg, 0.664 mmol) in anhydrous THF (2.0 mL) was cooled to −78° C. A solution of 1M LHMDS in THF (800 µL, 0.797 mmol) was added to the solution and the reaction was warmed to room temperature. MeI (63 µL, 0.996 mmol) was added to the reaction and stirred at ambient temperature for 72 hours. The reaction was partitioned between ethyl acetate and water and the organic layer was concentrated to give the subtitle compound that was purified by silica gel chromatography (EtOAc/Hex-gradient) prior to use in subsequent steps. MS: ESI (positive): 278 (M+Na).

c.) (R,S)-2-Bromo-4-methoxy-4,5,7,8-tetrahydro-thieno[2,3-d]azepine-6-carboxylic acid ethyl ester The subtitle compound was prepared by the method of Example 18, step d) using the product from step b).

d.) (R,S)-2-Bromo-4-methoxy-5,6,7,8-tetrahydro-4H-thieno[2,3-d]azepine

The title compound was prepared by the method described in Example 18, step e) using the product from step c). MS: ESI (positive): 262 (M+H).

EXAMPLE 34

2-Bromo-8,8-dimethyl-5,6,7,8-tetrahydro-4H-thieno[2,3-d]azepine (Scheme 7)

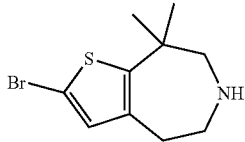

a.) 8,8-Dimethyl-4,5,7,8-tetrahydro-thieno[2,3-d]azepine-6-carboxylic acid ethyl ester DCM (5 mL) was cooled to −78° C. and treated with TiCl$_4$ (274 uL, 2.5 mmol) followed by Me$_2$Zn (1.3 mL of 2M solution in toluene). After stirring the dark red solution at −78° C. for 15 minutes, the product of Example 24, step d) (100 mg, 0.42 mmol) was added slowly as a solution in 5 mL DCM. The reaction was warmed to 0° C. and stirred for 2 hours. The reaction was quenched over ice and the product was extracted into DCM (2×). The organic extracts were dried over MgSO$_4$ and concentrated to give the subtitle compound, which was used without further purification.

b.) 2-Bromo-8,8-dimethyl-5,6,7,8-tetrahydro-4H-thieno[2,3-d]azepine

The product of step a) (45 mg, 0.18 mmol) was dissolved in 4 mL of 1:1HOAc/CHCl$_3$ and treated with NBS (44 mg, 0.25 mmol). After stirring for ½ hour, the reaction was concentrated to dryness and treated with 2 mL each of EtOH and 40% aqueous KOH. The mixture was heated to 100° C. overnight, cooled, and diluted with water. The product was extracted 2× into DCM (2×4 mL), concentrated, and purified by preparative HPLC-MS. $^1$H NMR (CD$_3$OD) δ 7.19 (s, 1H), 3.40-3.34 (m, 2H), 3.28 (s, 2H), 3.21-3.17 (m, 2H), 1.41 (s, 6H); MS: ESI (positive): 260, 262 (M+H).

EXAMPLE 35

(R,S)-2-Bromo-4-ethyl-5,6,7,8-tetrahydro-4H-thieno[2,3-d]azepine (Scheme 9)

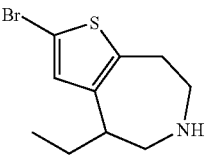

a.) (E,Z)-4-Ethylidene-4,5,7,8-tetrahydro-thieno[2,3-d]azepine-6-carboxylic acid ethyl ester KHMDS (233 mg, 1.17 mmol) was added to a solution of(Ethyl)triphenylphosphonium bromide (466 mg, 1.26 mmol) in THF (5 mL) cooled to 0° C. and the resultant solution was stirred for 20 minutes. The product from Example 1, step c) (200 mg, 0.837 mmol) in THF (5 mL) was added to the reaction and the reaction was warmed to ambient temperature over 1 hour. The reaction was quenched with water and partitioned between ethyl acetate and water. The organic layer was concentrated and the crude product was purified by silica gel chromatography (EtOAc/Hex-gradient) to give 151 mg of the subtitle compound as a mixture of the E and Z iosmers. MS: ESI (positive): 252 (M+H).

b.) (R,S)-4-Ethyl-4,5,7,8-tetrahydro-thieno[2,3-d]azepine-6-carboxylic acid ethyl ester The product of step a) (151 mg, 0.602 mmol) was stirred with 10% Pd/C (50 mg) in ethanol (3 mL) under H$_2$ (1 atm) for overnight. The reaction was filtered over celite and concentrated to dryness to give the 131 mg of the subtitle compound as a purple oil that was used without further purification. MS: ESI (positive): 254 (M+H).

c.) (R,S)-2-Bromo-4-ethyl-4,5,7,8-tetrahydro-thieno[2,3-d]azepine-6-carboxylic acid ethyl ester The subtitle compound was prepared by the method of Example 18, step d) using the product from step b) and was used in crude form without purification.

d.) (R,S)-2-Bromo-4-ethyl-5,6,7,8-tetrahydro-4H-thieno[2,3-d]azepine

The title compound was prepared by the method described in Example 18, step e) using the product from example step c). $^1$H NMR (CD$_3$OD) δ 6.88 (s, 1H), 3.19-3.28 (m, 3H), 2.92-3.15 (m, 4H), 1.61-1.84 (m, 2H), 0.98 (t, J=7.3 Hz, 3H). MS: ESI (positive): 260 (M+H).

EXAMPLE 36

2-Bromo-3,4-dimethyl-5,6,7,8-tetrahydro-4H-thieno[2,3-d]azepine (Scheme 9)

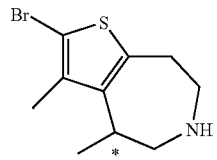

a.) 3-Bromo-4-methyl-4,5,7,8-tetrahydro-thieno[2,3-d]azepine-6-carboxylic acid ethyl ester The product of Example 23, step c) (enantiomer 2, 0.75 g, 1.9 mmol) and Zn (0.25 g, 3.8 mmol) were heated to reflux in 20 mL each water and HOAc. After ½ hour, the reaction was cooled, diluted with EtOAc, and washed 2× with water. The organic layer was dried over $MgSO_4$ and concentrated to give 490 mg of the subtitle compound as an oil, which was used without further purification.

b.) 3,4-Dimethyl-4,5,7,8-tetrahydro-thieno[2,3-d]azepine-6-carboxylic acid ethyl ester The product of step a) (150 mg, 0.47 mmol) was dissolved in 3 mL dioxane and treated with $Me_2Zn$ (0.47 mL of 2M in toluene) and $Pd(ddf)_2Cl_2$ (11 mg, 0.014 mmol). After heating to 100° C. for 3 hours, the reaction was quenched with water and filtered. The filtrate was partitioned between EtOAc and water (7 mL each). The organic layer was dried over MgSO4 and concentrated to give 92 mg of the subtitle compound, which was used without further purification.

c.) 2-Bromo-3,4-dimethyl-4,5,7,8-tetrahydro-thieno[2,3-d]azepine-6-carboxylic acid ethyl ester The product of step b) (92 mg, 0.36 mmol) was dissolved in 4 mL of 1:1HOAc/$CHCl_3$and treated with NBS (67 mg, 0.38 mmol). After stirring for ½ hour, the reaction was diluted with EtOAc (70 mL), washed with water (3×30 mL), and 1M NaOH (2×30 mL). The organic solution was dried over $MgSO_4$ and concentrated. The crude product was purified by silica gel chromatography (EtOAc/Hex-gradient) to give 90 mg of the subtitle compound.

d.) 2-Bromo-3,4-dimethyl-5,6,7,8-tetrahydro-4H-thieno[2,3-d]azepine

The product of step c) was deprotected as described for Example 20, step b). The title compound was obtained after purification by preparative HPLC-MS. 1H NMR ($CD_3OD$) δ 3.59-3.08 (m, 7H), 2.13 (s, 3H), 1.31 (d, J=7.2 Hz, 3H); MS: ESI (positive): 260, 262 (M+H).

*Enantiomer 1 can be prepared in a similar fashion.

EXAMPLE 37

2-Bromo-4,4a,5,6,7,8-hexahydro-3H-1-thia-6-aza-cyclopenta[cd]azulene (Scheme 10)

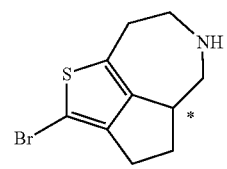

a.) (E,Z)-4-Ethoxycarbonylmethylene-4,5,7,8-tetrahydro-thieno[2,3-d]azepine-6-carboxylic acid ethyl ester To a solution of triethyl phosphonoacetate (4 mL, 16.74 mmol) in anhydrous THF (100 mL) was added a 1.6M LHMDS solution in THF (15 mL). The mixture was stirred at for 15 minutes followed by the addition of product from Example 1, step c) (2.0 g, 8.37 mmol). The reaction was stirred overnight then treated with additional LHMDS solution (3.2 mL of 1.6 M) and triethylphosphonoacetate (800 µL, 3.3 mmol). After stirring 3 hours, the reaction was quenched with water and diluted with DCM. The organic layer was dried over $MgSO_4$ and concentrated to give the subtitle compound, which was used without further purification. MS: ESI (positive): 310 (M+H).

b.) (R,S)-4-Ethoxycarbonylmethyl-4,5,7,8-tetrahydro-thieno[2,3-d]azepine-6-carbokylic acid ethyl ester The product of step a) (2.47 g, 8 mmol) was stirred with 2.0 g of 10% Pd/C (wet, Degussa grade E101) in methanol (8 mL) under $H_2$ (1 atm) for 72 hours. The reaction was filtered over celite and concentrated to dryness to give the subtitle compound as an oil, which was used without further purification. MS: ESI (positive): 312 (M+H).

c.) (R,S)-4-Carboxymethyl-4,5,7,8-tetrahydro-thieno[2,3-d]azepine-6-carboxylic acid ethyl ester The product of step b) (2.47 g, 8 mmol) was stirred in ethanol (60 mL) with 1M NaOH (30 mL) at ambient temperature overnight. The reaction was acidified with 1M HCl and partitioned between DCM and water. The organic layer was washed with water, dried over $MgSO_4$, and concentrated to dryness to give the 2.13 g of the subtitle compound as a yellow oil, which was used without further purification. MS: ESI (positive): 284 (M+H).

d.) (R,S)-3-Oxo-3,4,4a,5,7,8-hexahydro-1-thia-6-aza-cyclopenta[cd]azulene-6-carboxylic acid ethyl ester Oxalyl chloride (3 mL, 37.7 mmol) and a catalytic amount of DMF were added to a solution of the product from step c) (2.13 g, 7.54 mmol) in DCM (40 mL) and the reaction was stirred at ambient temperature for 1 hour. The reaction was concentrated to dryness and redissolved in dichloroethane (100 mL). $AlCl_3$ (2.0 g, 15.1 mmol) was added to the solution and the reaction was stirred at ambient temperature overnight. The reaction was quenched with ice and partitioned between DCM and water. The organic layer was concentrated to give the subtitle compound, which was purified by silica gel chromatography (EtOAc/Hex-gradient, isolated 1.02 g) prior to use in subsequent steps. MS: ESI (positive): 266 (M+H).

e.) (R,S)-3,4,4a,5,7,8-Hexahydro-1-thia-6-aza-cyclopenta[cd]azulene-6-carboxylic acid ethyl ester $AlCl_3$ (627 mg, 4.72 mmol) was added to $BH_3tBuNH_2$ (492 mg, 5.66 mmol) in DCM (2 mL) at 0° C. The solution was stirred for 10 minutes then treated with the product from step d) (250 mg, 0.943 mmol) as a solution in DCM (1 mL). After warming to rt, the reaction was quenched with 0.1M. HCl dropwise and concentrated to dryness. The reaction was diluted in 1M HCl and extracted into EtOAc. The organic layer was concentrated to give the sub-title compound, which was purified by silica gel chromatography (EtOAc/Hex-gradient) prior to use in subsequent steps. MS: ESI (positive): 252 (M+H).

f.) (R,S)-2-Bromo-3,4,4a,5,7,8-hexahydro-1-thia-6-aza-cyclopenta[cd]azulene-6-carboxylic acid ethyl ester The sub-title compound was prepared by the method of Example 18, step d) using the product from step e) and was used in crude form without purification.

g.) 2-Bromo-4,4a,5,6,7,8-hexahydro-3H-1-thia-6-aza-cyclopenta[cd]azulene

The title compound was prepared by the method described in Example 18, step e) using the product from step f) and purified by preparative HPLC-MS. The two enantiomers were separated using a Chiralpak® AD-RH> 20×250 mm column from Chiral Technologies (10 mL/min MeOH mobile phase) to give enantiomer 1 (rt=8.6 minutes) and enantiomer 2 (rt=10.8 minutes) of the title compound. $^1$H NMR ($CD_3OD$) δ 3.45-3.56 (m, 2H), 2.89-3.08 (m, 3H), 2.45-2.65 (m, 4H), 1.99-2.04 (m, 2H). MS: ESI (positive): 260 (M+H).

EXAMPLE 38

(R,S)-2-Methyl-4,4a,5,6,7,8-hexahydro-3H-1-thia-6-aza-cyclopenta[cd]azulene: (Scheme 10)

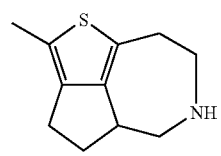

a.) (R,S)-2-Methyl-3,4,4a,5,7,8-hexahydro-1-thia-6-aza-cyclopenta[cd]azulene-6-carboxylic acid ethyl ester A solution of 2M $Me_2Zn$ in toluene (1.5 mL) was added to the product from Example 37, step f) (50 mg, 0.150 mmol) and $Pd(dppf)_2Cl_2$ (4 mg, 0.0045 mmol) in dioxane (1 mL). After heating to 100° C. for 3 hours, the reaction was quenched with water and extracted into ethyl acetate. The organic layers were combined and concentrated to give the subtitle compound that was used in crude form without purification. MS: ESI (positive): 266 (M+H).

b.) (R,S)-2-Methyl-4,4a,5,6,7,8-hexahydro-3H-1-thia-6-aza-cyclopenta[cd]azulene The title compound was prepared by the method described in Example 18, step e) using the product from step a) and purified by preparative HPLC-MS. $^1$H NMR ($CD_3OD$) δ 3.52-3.64 (m, 21H), 3.25-3.30 (m, 1H), 2.86-3.10 (m, 4H), 2.46-2.73 (m, 4H), 2.23 (s, 3H). MS: ESI (positive): 194 (M+H).

EXAMPLE 39

2-tert-Butyl-4,4a,5,6,7,8-hexahydro-3H-1-thia-6-aza-cyclopenta[cd]azulene: (Scheme 10)

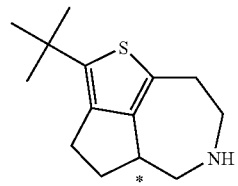

a.) (R,S)-2-tert-Butyl-3,4,4a,5,7,8-hexahydro-1-thia-6-aza-cyclopenta[cd]azulene-6-carboxylic acid ethyl ester The product from Example 37, step e) (100 mg, 0.398 mmol), $BF_3$-OEt (50 μL, 0.398 mmol), and tert-butanol (56 μL, 0.597 mmol) were heated to 75° C. for 2 hours in dichloroethane (1 mL). The reaction was quenched with water and extracted into DCM. The organic layers were combined and concentrated overnight to give the subtitle compound that was used in crude form without purification. MS: ESI (positive): 308 (M+H).

b.) 2-tert-Butyl-4,4a,5,6,7,8-hexahydro-3H-1-thia-6-aza-cyclopenta[cd]azulene The title compound was prepared by the method described in Example 18, step e) using the product from step a). The two enantiomers were separated using a Chiralpak® AD-RH® 20×250 mm column from Chiral Technologies (10 mL/min MeOH mobile phase) to give enantiomer 1 (rt=7.7 minutes) and enantiomer 2 (rt=10.2 minutes) of the title compound. $^1$H NMR ($CD_3OD$) δ 3.20-3.34 (m, 2H), 2.91-3.01 (m, 1H), 2.56-2.91 (m, 5H), 2.27-2.39 (m, 2H), 1.74-1.88 (m, 1H), 1.30 (s, 9H). MS: ESI (positive): 236 (M+H).

EXAMPLE 40

2-Trifluoromethyl-5,6,7,8-tetrahydro-4H-thieno[2,3-d]azepine (Scheme 1a)

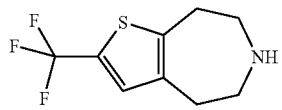

a.) 2-Iodo-4,5,7,8-tetrahydro-thieno[2,3-d]azepine-6-carboxylic acid ethyl ester A solution of the product from Example 1, step d) (470 mg, 2.09 mmol) in CHCl$_3$ (5 ml) and AcOH (5 ml) was treated with N-iodosuccinimide (493 mg, 2.19 mmol) at 22° C. After 1 hour, the reaction was diluted with CH$_2$Cl$_2$ (20 ml) and poured into sat. NaHCO$_3$ (20 ml). The organic layer was washed with brine (1×20 ml), dried (MgSO$_4$) and concentrated providing the crude subtitle compound as a yellow oil, which was used without further purification.

b.) 2-Trifluoromethyl-4,5,7,8-tetrahydro-thieno[2,3-d]azepine-6-carboxylic acid ethyl ester A solution of the product from step a.) (75 mg, 0.21 mmol) in DMF (0.5 ml) and NMP (0.5 ml) was treated with bipyridyl (43 mg, 0.27 mmol), CuI (44 mg, 0.23 mmol), KF (13 mg, 0.23 mmol) and trimethylsilyltrifluoromethane (2.1 ml, 1.05 mmol). The reaction mixture was heated to 80° C. for 3 days. The reaction was cooled and filtered through celite washing with EtOAc (20 ml). The eluent was washed with brine (2×3 ml) and dried (MgSO$_4$) providing the subtitle compound as a brown oil that was used without further purification.

c.) 2-Trifluoromethyl-5,6,7,8-tetrahydro-4H-thieno[2,3-d]azepine

A solution of the crude product from step b.) (26 mg, 0.089 mmol) in CH$_2$Cl$_2$ (0.5 ml) was treated with iodotrimethylsilane (19 µl, 0.134 mmol) at 50° C. for 12 hours. The reaction was quenched by the addition of MeOH and the solvent was evaporated. The residue was purified by preparative LC/MS providing the title compound. NMR (300 MHz, CDCl$_3$) δ 7.18 (s, 1 H); 3.42-3.56 (m, 6H); 3.31-3.39 (m, 2H), 2.09 (s, 1H); MS: ESI (positive): 222 (M+H).

EXAMPLE 41

3-Chloro-2-trifluoromethyl-5,6,7,8-tetrahydro-4H-thieno[2,3-d]azepine (Scheme 1b)

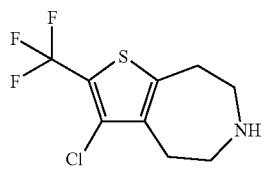

a.) 2,3-Dichloro-4,5,7,8-tetrahydro-thieno[2,3-d]azepine-6-carboxylic acid ethyl ester A solution of the product from Example 4, step H) (323 mg, 1.25 mmol) in CH$_2$Cl$_2$ (6.25 ml) was cooled to 0° C. and triethylamine (522 µl, 3.75 mmol) was added followed by ethylchloroformate (144 µl, 1.5 mmol). After 1.5 hours the reaction was poured into water (25 ml) and diluted with EtOAc (50 ml). The organic layer was dried (MgSO$_4$) and concentrated providing 341 mg (93%) of the subtitle compound that was used without further purification. MS: ESI (positive): 294, 296 (M+H).

b.) 3-Chloro-2-iodo-4,5,7,8-tetrahydro-thieno[2,3-d]azepine-6-carboxylic acid ethyl ester A solution of the product from step a) (129 mg, 0.44 mmol) in anhydrous THF (2.2 ml) was cooled to −78° C. and treated with 1.5 equiv of n-BuLi (412 µl, 0.66 mmol). After 1 h, the reaction was quenched with a THF solution of I$_2$ (167 mg, 0.66 mmol). The reaction was warmed to 22° C. and diluted with EtOAc (15 ml). The organic layer was washed with sat. NaSO$_3$ (5 ml), brine (5 ml) and dried (MgSO$_4$) providing 98 mg (58%) of the crude subtitled compound that was used without further purification. MS: ESI (positive): 386 (M+H).

c.) 3-Chloro-2-trifluoromethyl-4,5,7,8-tetrahydro-thieno[2,3-d]azepine-6-carboxylic acid ethyl ester A solution of the product from step b) (140 mg, 0.363 mmol) in NMP (0.9 ml) and DMF (0.9 ml) was treated with CuI (76 mg, 0.39 mmol), KF (46.4 mg, 0.79 mmol), bipyridyl (74 mg, 0.472 mmol) and TMSCF$_3$ (267 µl, 1.81 mmol). The mixture was heated to 80° C. for 12 hours. The crude reaction mixture was diluted with EtOAc and filtered through celite. The organic phase was washed with H$_2$O (2×1 ml), brine (1×1 ml), dried (MgSO$_4$) and concentrated. The crude product was purified by preparative TLC using 10:1 hexanes/EtOAc providing 14.4 mg (12.1%) of the subtitle compound.

d.) 3-Chloro-2-trifluoromethyl-5,6,7,8-tetrahydro-4H-thieno[2,3-d]azepine

A solution of the product from step c) (14.4 mg, 0.044 mmol) in CH$_2$Cl$_2$ (220 µl) was treated with iodotrimethylsilane (19 µl, 0.13 mmol) at 60° C. for 12 hours. The reaction was quenched by the addition of MeOH and the solvent was evaporated. The residue was purified by preparative LC/MS providing 2.3 mg (18%) of the title compound. MS: ESI (positive): 256 (M+H).

EXAMPLE 42

3-Bromo-2-trifluoromethyl-5,6,7,8-tetrahydro-4H-thieno[2,3-d]azepine (Scheme 1b)

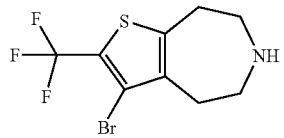

a.) 3-Bromo-4,5,7,8-tetrahydro-thieno[2,3-d]azepine-6-carboxylic acid ethyl ester A solution of the product from example 3, step a) (148 mg, 0.39 mmol) in AcOH (80 μl) and H$_2$O (1.92 ml) was treated with Zn (76 mg, 1.17 mmol) at 105° C. for 4.5 hours. Next, the contents were cooled to 22° C., poured into sat. NaHCO$_3$ (25 ml) and extracted with EtOAc (2×25 ml). The organic layer was dried (MgSO$_4$) and concentrated providing 80 mg (68%) of the subtitle compound, which was used without further purification.

b.) 3-Bromo-2-iodo-4,5,7,8-tetrahydro-thieno[2,3-d]azepine-6-carboxylic acid ethyl ester A solution of the product from step a) (124 mg, 0.41 mmol) in CHCl$_3$ (1.0 ml) and AcOH (1.0 ml) was treated with N-iodosuccinimide (97 mg, 0.43 mmol) for 30 minutes. Next, the crude reaction was poured into sat. NaHCO$_3$ (5 ml) and extracted with CH$_2$Cl$_2$ (2×4 ml). The organic layer was washed with sat. NaHCO$_3$ (3 ml), dried (extrelut column), concentrated and purified by preparative TLC (80% hexanes: 20% EtOAc) providing 134 mg (76%) of the subtitle compound.

c.) 3-Bromo-2-trifluoromethyl-4,5,7,8-tetrahydro-thieno[2,3-d]azepine-6-carboxylic acid ethyl ester A solution of the product from step b) (134 mg, 0.31 mmol) in NMP (1 ml) and DMF (1 ml) was treated with KF (20 mg, 0.34 mmol), CuI (65 mg, 0.34 mmol) and bipyridyl (62 mg, 0.4 mmol) at 50° C. for 15 minutes. Next, a 0.5 M solution of trimethylsilyltrifluoro-methane (3.1 ml, 1.55 mmol) was added and the reaction mixture was stirred 16 hours at 80° C. The reaction mixture was cooled to 22° C., diluted with CH$_2$Cl$_2$ (5 ml) and washed with brine (10 ml). The aqueous layer was extracted with CH$_2$Cl$_2$ (3×5 ml) and the combined organic layers were dried (extrelut column), passed through a plug of silica gel, concentrated and purified by preparative LC/MS providing 26 mg (23%) of the subtitle compound.

d.) 3-Bromo-2-trifluoromethyl-5,6,7,8-tetrahydro-4H-thieno[2,3-d]azepine

A solution of the product from step c) (51 mg, 0.137 mmol) in CH$_2$Cl$_2$ (685 μl) was treated with iodotrimethylsilane (59 μl) at 50° C. for 16 hours. The reaction was quenched by the addition of MeOH and the solvent was evaporated. The residue was purified by preparative LC/MS providing 16 mg (39%) of the title compound. NMR (300 MHz, CDCl$_3$) δ 4.10-4.40 (br s, 1H); 2.90-3.60 (m, 8H). MS: ESI (positive): 300, 302 (M+H).

EXAMPLE 43

3-Methyl-5,6,7,8-tetrahydro-4H-thieno[2,3-d]azepine (Scheme 3)

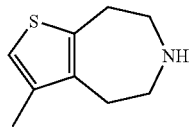

a.) 3-Methyl-4,5,7,8-tetrahydro-thieno[2,3-d]azepine-6-carboxylic acid ethyl ester A solution of the product from Example 42, step a) (122 mg, 0.40 mmol) in dry THF (2 ml) was treated with NiCl$_2$ (dppp) (2-3 mg, 0.004 mmol) followed by dropwise addition of a 1.4 M solution of methylmagnesium bromide (0.71 ml, 1 mmol) at 22° C. and then the reaction was refluxed for 16 hours. The reaction mixture was cooled to 22° C., diluted with ether (5 ml), and quenched with 1N HCl (2 ml). The aqueous layer was back extracted with ether (3×5 ml). The combined organic extracts were washed with water (10 ml) and dried (MgSO$_4$). The solvent was evaporated giving the crude subtitle compound as a tan oil, which was used without further purification.

b.) 3-Methyl-5,6,7,8-tetrahydro-4H-thieno[2,3-d]azepine

A solution of the product from step a) in CH$_2$Cl$_2$ (1 ml) was treated with iodotrimethylsilane at 50° C. for 16 hours. The reaction was quenched by the addition of MeOH and the solvent was evaporated. The residue was purified by preparative LC/MS providing 1.6 mg of the title compound. NMR (300 MHz, CDCl$_3$) δ 6.69 (d, J=1 Hz, 1H); 4.8-5.2 (br s, 1H); 3.20-3.40 (m, 6H); 3.00-3.1 (m, 2H); 2.14 (d, J=1 Hz, 3H); MS: ESI (positive): 168 (M+H).

EXAMPLE 44

2-tert-Butyl-3-methoxy-5,6,7,8-tetrahydro-4H-thieno[2,3-d]azepine (Scheme 5)

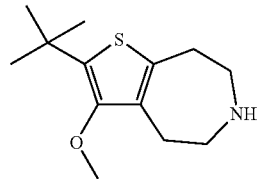

a.) 2-tert-Butyl-3-methyl-4,5,7,8-tetrahydro-thieno[2,3-d]azepine-6-carboxylic acid ethyl ester To a stirred solution of the product of Example 18, step a) (20 mg, 0.078 mmol) in 0.5 mL DCE was added t-Butanol (25 uL, 0.26 mmol) followed by BF$_3$-OEt$_2$ (10 uL, 0.078 mmol). The reaction was heated to 75° C. for 2 hours. The reaction was allowed to cool to room temperature, concentrated to dryness, and the residue used without further purification. MS: ESI (positive): 312 (M+H).

b.) 2-tert-Butyl-3-methyl-5,6,7,8-tetrahydro-4H-thieno[2,3-d]azepine

The product of step a) was treated with 0.5 mL each of EtOH and 40% aqueous KOH. After heating to 100° C. for 18 hours, the reaction was cooled, diluted with water, and extracted into DCM (2×10 ml). The organic layer was concentrated to dryness and the residue purified by preparative HPLC-MS to give the title compound. $^1$H NMR (300 MHz, CD$_3$OD) δ 3.78 (s, 3H); 3.30-3.38 (m, 4H); 3.06-3.15 (m, 2H); 2.94-3.03 (m, 2H); 1.45 (s, 9H). MS: ESI (positive): 240 (M+H).

EXAMPLE 45

2-tert-Butyl-5,6,7,8-tetrahydro-4H-thieno[2,3-d]azepine (Scheme 9)

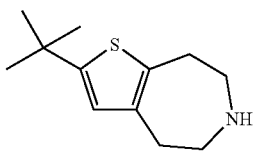

To a stirred solution of the product from Example 1, step d) (66 mg, 0.29 mmol) in 2.5 mL of DCE was added t-Butanol (36 uL, 0.38 mmol) and $BF_3$-$OEt_2$ (36 uL, 0.29 mmol). The reaction was heated to 60° C. for 2 hours. The reaction was concentrated to dryness and treated with 2 mL each of EtOH and 40% aqueous KOH. The mixture was heated to 100° C. overnight, cooled, and diluted with water. The product was extracted into DCM (2×10 mL), concentrated, and purified by preparative HPLC-MS to give the title compound. MS: ESI (positive): 210 (M+H).

EXAMPLE 46

2-tert-Butyl-3-chloro-5,6,7,8-tetrahydro-4H-thieno[2,3-d]azepine (Scheme 4)

EXAMPLE 47

3-Chloro-2-(1,1,3,3-tetramethyl-butyl)-5,6,7,8-tetrahydro-4H-thieno[2,3-d]azepine (Scheme 4)

EXAMPLE 48

3-Chloro-5,6,7,8-tetrahydro-4H-thieno[2,3-d]azepine (Scheme 4)

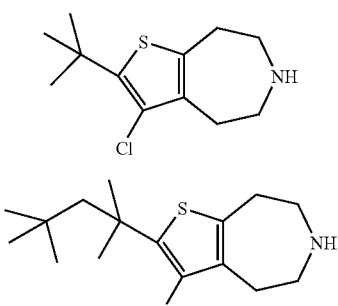

Example 46

Example 47

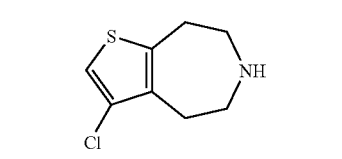

Example 48 a.) 3-Chloro-4,5,7,8-tetrahydro-thieno[2,3-d]azepine-6-carboxylic acid ethyl ester A solution of the product from Example 41 step a.) (382 mg, 1.3 mmol) in THF (6.5 ml) was cooled to −78° C. and treated with a 1.6 M solution of n-BuLi (2.26 ml, 1.36 mmol). After 1 hour, the reaction was quenched with water and extracted with EtOAc (2×30 ml). The organic layer was washed with brine (1×15 ml), dried ($MgSO_4$) and concentrated. The crude yellow oil was purified by silica gel chromatography (EtOAc/Hexane-gradient) providing 156 mg (46%) of the subtitle compound. $^1$H NMR (300 MHz, $CDCl_3$) δ 6.88 (s, 1H); 4.19 (q, J=7 Hz, 2H); 3.57-3.72 (m, 4H); 2.92-3.03 (m, 2H); 2.81-2.92 (m, 2H); 1.29 (t, J=7 Hz, 3 H).

b.) 2-tert-Butyl-3-chloro-4,5,7,8-tetrahydro-thieno[2,3-d]azepine-6-carboxylic acid ethyl ester A solution of the product from step a.) (156 mg, 0.6 mmol) in dichloroethane (3 ml) was treated with t-BuOH (172 μl, 1.8 mmol) and $BF_3$-$OEt_2$ (113 μl, 0.9 mmol). The reaction mixture was heated at 85° C. for 6 hours followed by evaporation of the solvent providing the crude subtitle compound.

c.) 2-tert-Butyl-3-chloro-5,6,7,8-tetrahydro-4H-thieno[2,3-d]azepine

EXAMPLE 44

3-Chloro-2-(1,1,3,3-tetramethyl-butyl)-5,6,7,8-tetrahydro-4H-thieno[2,3-d]azepine

EXAMPLE 45

3-Chloro-5,6,7,8-tetrahydro-4H-thieno[2,3-d]azepine

EXAMPLE 46

A solution of the crude product from step b.) in EtOH (4 ml) and 40% aqueous KOH (4 ml) was treated with tetra-butylammonium bromide (20 mg) and heated to 95° C. for 2 days. Next, the reaction was cooled to 22° C. and extracted with $CH_2Cl_2$ (3×25 ml). The organic layer was washed with brine (1×10 ml), dried ($MgSO_4$), and concentrated to dryness. The residue was purified by preparative LC/MS providing the subtitle compounds. (A) $^1$H NMR (300 MHz, $CDCl_3$) δ0 6.50-6.80 (br s, 1H); 3.05-3.14 (m, 4H); 2.87-2.99 (m, 4H); 1.43 (s, 9 H); MS: ESI (positive): 244 (M+H); (B) $^1$H NMR (300 MHz, $CDCl_3$) δ 3.58-3.70 (br s, 1H); 2.98-3.09 (m, 4H); 2.88-2.94 (m, 2H); 2.82-2.87 (m, 2H); 1.91 (s, 2H); 1.46 (s, 6H); 0.81 (s, 9H); MS: ESI (positive): 300 (M+H); (C) $^1$H NMR (300 MHz, $CDCl_3$) δ 6.75 (s, 1H); 2.92-3.11 (m, 6H); 2.85-2.90 (m, 2H); 2.72-2.82 (br s, 1H); MS: ESI (positive): 188 (M+H).

EXAMPLE 49

2-Bromo-5,6,7,8-tetrahydro-4H-furo[2,3-d]azepine (Scheme 11)

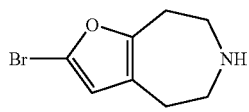

a.) Furan-2-yl-oxo-acetic acid ethyl ester

Furan-2-yl-oxo-acetic acid (15 g, 107 mmol), dissolved in $CHCl_3$ (420 ml), was treated with EtOH (9.6 ml, 165 mmol)

and $H_2SO_4$ (1 ml) and heated to 63° C. for 12 hours. Next, the reaction mixture was transferred to a separatory funnel and washed with sat. $NaHCO_3$ (100 ml). The organic layer was washed with brine (100 ml), dried ($MgSO_4$) and concentrated providing 16.9 g (66%) of the above subtitle compound, which was carried forward without further purification.

b.) Furan-2-yl-hydroxy-acetic acid

A solution of the product from step a.) (25 g, 135 mmol) in EtOH (250 ml) was cooled to 0° C. and treated with a solution of $NaBH_4$ (2.5 g, 66 mmol) in $H_2O$ (27 ml) for 5 minutes. Next, the reaction mixture was quenched with AcOH (17 ml) and $H_2O$ (271 ml) and concentrated to dryness. The crude oil was dissolved in $CH_2Cl_2$ (300 ml), washed with brine (2×100 ml), dried ($MgSO_4$) and concentrated providing 17.5 g (70%) of the above subtitle compound, which was carried forward without further purification.

c.) (3-Carboxymethyl-furan-2-yl)-acetic acid

A solution of the product from step b.) (10.9 g, 64 mmol) in decalin (193 ml) was treated with trimethylorthoacetate (48.2 ml, 384 mmol) and hexanoic acid (2.0 ml). Next, the reaction mixture was fitted with a Vigreaux column and heated to 180° C. for 18 hours. Additional hexanoic acid (3×1.5 ml) aliquots of hexanoic acid were added every 2 hours for the first 6 hours of reaction time. Next, the reaction was cooled to 22° C. and extracted with MeOH providing 27 g of a crude mixture of the diester and decalin. This mixture was dissolved in MeOH (250 ml), cooled to 0° C., and treated with 2 M NaOH (150 ml). After 12 hours, the solvent was evaporated and the residue was taken up in 2 N NaOH (100 ml) and washed with ether (2×150 ml). The basic layer was acidified with 4 M HCl to pH 1 and back extracted with EtOAc (4×100 ml). The organic layer was washed with brine, dried ($MgSO_4$) and concentrated providing 6.4 g (54%) of the above subtitle compound.

d.) 2-[3-(2-Hydroxy-ethyl)-furan-2-yl]-ethanol

A solution of the product from step c.) (6.4 g, 35 mmol) in dry THF (400 ml) was cooled to 0° C. and a 1.0 M solution of $BH_3$ in THF (174 ml, 174 mmol) was added dropwise over 10 minutes. After the addition was complete the mixture was stirred for an additional 20 minutes at 0° C. and then warmed to 22° C. for 2 hours. Next, the mixture was poured into ice cold sat. $NaHCO_3$ (300 ml) and extracted with EtOAc (2×200 ml). The organic layer was dried ($MgSO_4$) and concentrated providing 3.58 g (65%) of the subtitle compound. MS: ESI (positive): 157 (M+H).

e.) Methanesulfonic acid 2-[3-(2-methanesulfonyloxy-ethyl)-furan-2-yl]-ethyl ester A solution of the product from step d.) (3.58 g, 22.9 mmol) in $CH_2Cl_2$ (114 ml), was cooled to 0° C., and treated with triethylamine (9.56 ml, 68.7 mmol) followed by dropwise addition of methanesulfonyl chloride (3.88 ml, 50.4 mmol) over 10 minutes. After 1 hour, the reaction mixture was transferred to a separatory funnel and extracted with ice water (1×50 ml), 10% citric acid (2×50 ml), sat. $NaHCO_3$ (2×50 ml) and brine (1×50 ml). The organic layer was dried ($MgSO_4$), concentrated to 20 ml, diluted with dry dioxane (42 ml) and further concentrated to remove remaining $CH_2Cl_2$. The resulting dioxane solution of the bismesylate was immediately carried into step f)

f.) 6-Benzyl-5,6,7,8-tetrahydro-4H-furo[2,3-d]azepine

The bismesylate dioxane solution, generated in step e), was diluted with dry dioxane (168 ml) and transferred to a 3-neck reaction flask equipped with a dropping funnel and condenser. Anhydrous $K_2CO_3$ (46.5 g, 337 mmol) was added and the mixture was heated to 102° C. Next, a solution of benzylamine (7.5 g, 70.1 mmol) in dioxane (74.4 ml) was added dropwise over 45 minutes and the reaction was refluxed for 18 hours. The mixture was cooled to 22° C., the salts were filtered off, and the solvent was evaporated. The crude oil was purified by silica gel chromatography (EtOAc/Hexane-gradient) providing 2.56 g (49%) (combined yield over steps e and f) of the subtitle compound. MS: ESI (positive): 228 (M+H).

g.) 5,6,7,8-Tetrahydro-4H-furo[2,3-d]azepine Hydrochloride

A solution of the product from step f) (2.56 mg, 11.3 mmol) in anhydrous dichloroethane (56 ml) was cooled to 0° C., treated with 1-chloroethyl chloroformate (6.11 ml, 56.4 mmol) and the reaction was warmed to 22° C. for 1 hour. The reaction was diluted with $CH_2Cl_2$ (100 ml) and washed with sat. $NaHCO_3$ (50 ml). The sat $NaHCO_3$ was back extracted with $CH_2Cl_2$ and the combined organic layers were washed with brine (50 ml), dried ($MgSO_4$) and concentrated providing an oily residue, which was taken up in anhydrous MeOH (150 ml) and refluxed for 1 hour. The MeOH was evaporated and the crude was triturated with ether and filtered providing 1.71 g (87%) of the subtitle compound. $^1$H NMR (300 MHz, DMSO) δ 9.56 (br s, 2H); 7.43 (d, J=2 Hz, 1H); 6.34 (d, J=2 Hz, 1H); 3.18-3.30 (br m, 4H); 3.03-3.10 (br m, 2H); 2.74-2.82 (br m, 2H); MS: ESI (positive): 138 (M+H).

h.) 4,5,7,8-Tetrahydro-furo[2,3-d]azepine-6-carboxylic acid tert-butyl ester

A solution of the product from step g) (500 mg, 2.88 mmol) in acetone (7.2 ml) and water (7.2 ml) was treated with $NaHCO_3$ (484 mg, 5.76 mmol) and di-tert-butyl dicarbonate (691 mg, 3.17 mmol) under vigorous stirring for 1 hour. The contents were diluted with $H_2O$ (10 ml) and extracted with EtOAc (2×50 ml). The organic layer was dried ($MgSO_4$), concentrated and purified by chromatography (EtOAc/Hexane-gradient) providing 643 mg (94%) of the subtitle compound. MS: ESI (positive): 238 (M+H).

i.) 2-Bromo-5,6,7,8-tetrahydro-4H-furo[2,3-d]azepine

A solution of the product from step h) (50 mg, 0.21 mmol) in $CHCl_3$ (527 µl) and AcOH (527 µl) was treated with N-bromosuccinimide (38.1 mg, 0.21 mmol) at 22° C. After 1 hour, the contents were poured into sat. $NaHCO_3$ and extracted with EtOAc (2×5 ml). The organic layer was washed with brine (1×5 ml), dried ($MgSO_4$) and purified by preparative TLC (80% hexanes:20% EtOAc) providing 2-bromo-4,5,7,8-tetrahydro-furo[2,3-d]azepine-6-carboxylic acid tert-butyl ester which was directly treated with 4M HCl in dioxane (2 ml). The dioxane was evaporated and the residue was dissolved in MeOH and purified by preparative LC/MS providing 1.3 mg of the title compound. $^1$H NMR ($CDCl_3$) 6.08 (s, 1H); 3.02-3.07 (m, 4H); 2.89-2.92 (m, 2H); 2.57-2.70 (m, 3H); MS: ESI (positive): 216, 218 (M+H).

The following procedure was utilized to evaluate representative compounds of the present invention as $5HT_{2c}$ receptor agonists. The results of this assay are set forth in Table 1.

Cell Culture

VNV Isoform: HEK 293 EBNA expressing the human 5HT2c receptor (Burns et al., NATURE 387:30308, 1997) were grown in DMEM containing 10% dialysed FBS, 9 ug/ml blasticidin at 37° C. in 5% $CO_2$ atmosphere.

Calcium Mobilization

HEK 293 EBNA cells expressing human $5HT2_c$ receptor ($2 \times 10^4$/well) were seeded in black 384-well collagen coated plates and incubated overnight at 37° C. in a 5% CO2/95% atmosphere. After removing medium, cells were treated with HBSS buffer (137 mM NaCl, 5.4 mM KCl, 5.5 mM Glucose, 20 mM Hepes, pH 7.5, 2.1 mM $MgCl_2$, 0.3 mM $CaCl_2$, 0.02 mM $MgSO_4$, 3.0 mM $NaHCO_3$, and 0.64 mM $KH_2PO_4$) containing the Calcium3 dye (Molecular Device, CA), 2.5 mM probenecid and 0.08% pluronic acid for 60 minutes according to manufacture's instruction. Compounds were diluted in CsCl Ringers buffer (58.3 mM CsCl, 5.4 mM KCl, 5.5 mM Glucose, 20 mM Hepes, pH 7.5, 2.1 mM $MgCl_2$, 1.2 mM $CaCl_2$). 5HT was utilized as a positive control. Ligand induced calcium release and consequent fluorescence was measured on a Fluorometric Imaging Plate Reader (FLIPR, Molecular Device, CA).

Data Analysis

All data were analyzed by nonlinear least square curve fitting using Prism 4.0 software. Agonist stimulation of calcium-induced fluorescence in FLIPR was fitted to sigmoidal dose response using equation Y=Bottom+(Top-Bottom)/(1+ 10^((Log EC50−X))), where X is the logarithm of concentration of compounds and Y is the fluorescent response.

TABLE 1

| Example Number | Molecule | 5-HT2c EC50 (hVSV, μM) |
| --- | --- | --- |
| 1 | Br-thieno-azepine | <0.01 |
| 2 | Cl-thieno-azepine | <0.1 |
| 3 | Br,Br-thieno-azepine | <0.01 |
| 4 | Cl,Cl-thieno-azepine | <0.01 |
| 5 | Br,Cl-thieno-azepine | <0.01 |
| 6 | F3C-O-phenyl-thieno-azepine | >10 |
| 7 | 2-CF3-phenyl-thieno-azepine | >10 |
| 8 | 4-F-phenyl-thieno-azepine | <10 |

TABLE 1-continued

| Example Number | Molecule | 5-HT2c EC50 (hVSV, μM) |
|---|---|---|
| 9 | | >10 |
| 10 | | >10 |
| 11 | | >10 |
| 12 | | <10 |
| 13 | | <10 |
| 14 | | <1 |
| 15 | | <10 |
| 16 | | <0.01 |
| 17 | | <0.01 |

TABLE 1-continued

| Example Number | Molecule | 5-HT2c EC50 (hVSV, μM) |
|---|---|---|
| 18 | (structure: 2-bromo-3-methoxy thieno-azepine) | <0.01 |
| 19 | (structure: 2-chloro-3-methoxy thieno-azepine) | <1 |
| 20 | (structure: 2-isopropenyl-3-methoxy thieno-azepine) | <0.01 |
| 21 | (structure: 2-tert-butyl-3-methyl thieno-azepine) | <0.1 |
| 22 | (structure: 2-isopropyl-3-methoxy thieno-azepine) | <0.01 |
| 23, Enantiomer 1 | (structure: 2-bromo-methyl thieno-azepine) | <0.1 |
| 23, Enantiomer 2 |  | <0.1 |
| 24, Enantiomer 1 | (structure: 2-bromo-methyl thieno-azepine) | <0.1 |
| 24, Enantiomer 2 |  | <0.1 |
| 25 | (structure: 2-bromo spiro-cyclopropyl thieno-azepine) | <1 |

TABLE 1-continued

| Example Number | Molecule | 5-HT2c EC50 (hVSV, μM) |
|---|---|---|
| 26 | | <0.01 |
| 27 | | <0.01 |
| 28 | | <0.01 |
| 29 | | <10 |
| 30 | | <1 |
| 31 | | <0.1 |
| 32, Enantiomer 1 | | <10 |
| 32, Enantiomer 2 | | <0.1 |
| 33 | | <1 |

TABLE 1-continued

| Example Number | Molecule | 5-HT2c EC50 (hVSV, μM) |
|---|---|---|
| 34 | | <10 |
| 35 | | <0.1 |
| 36, Enantiomer 1<br>36, Enantiomer 2 | | >10<br><1 |
| 37, Enantiomer 1<br>37, Enantiomer 2 | | <1<br><0.1 |
| 38 | | <1 |
| 39, Enantiomer 1<br>39, Enantiomer 2 | | <0.1<br><0.01 |
| 40 | | <0.01 |
| 41 | | <0.1 |
| 42 | | <0.01 |

TABLE 1-continued

| Example Number | Molecule | 5-HT2c EC50 (hVSV, µM) |
|---|---|---|
| 43 | 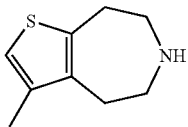 | <1 |
| 44 | 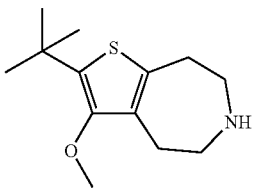 | <0.01 |
| 45 | 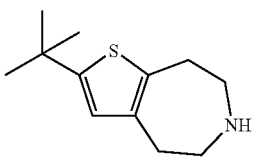 | <0.1 |
| 46 | 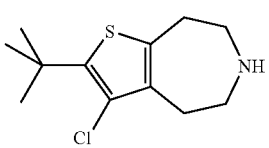 | <0.1 |
| 47 | 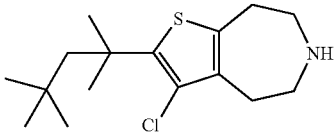 | <10 |
| 48 | 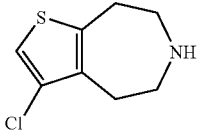 | <10 |
| 49 | 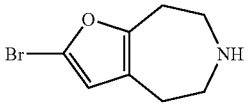 | <1 |

The invention claimed is:

1. A compound of the formula

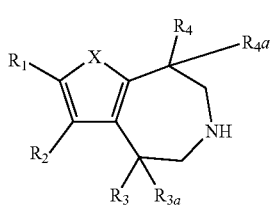

(I)

where:

X is S;

$R_1$ is selected from the group consisting of halogen, $C_{1-8}$ alkyl, $OR_5$, $SO_2N(R_5)_2$ and perhaloalkyl;

$R_2$ is selected from the group consisting of hydrogen, halogen, $C_{1-8}$ alkyl and $OR_5$, or together with $R_3$ forms a 5-membered ring;

$R_3$ is hydrogen or $C_{1-8}$ alkyl;

$R_{3a}$ is hydrogen;

$R_4$ is hydrogen or $C_{1-8}$ alkyl;

$R_{4a}$ is hydrogen; and $R_5$ is hydrogen or $C_{1-8}$ alkyl;

or a pharmaceutically acceptable salt thereof.

2. A compound selected from the group consisting of
2-Bromo-5,6,7,8-tetrahydro-4H-thieno[2,3-d]azepine;
2-Chloro-5,6,7,8-tetrahydro-4H-thieno[2,3-d]azepine;
2,3-Dibromo-5,6,7,8-tetrahydro-4H-thieno[2,3-d]azepine;
2,3-Dichloro-5,6,7,8-tetrahydro-4H-thieno[2,3-d]azepine;
2-Bromo-3-chloro-5,6,7,8-tetrahydro-4H-thieno[2,3-d]azepine;

2-Chloro-4-methoxy-5,6,7,8-tetrahydro-4H-thieno[2,3-d]azepine;
2-Chloro-4-methyl-5,6,7,8-tetrahydro-4H-thieno[2,3-d]azepine;
2,3-Dichloro-4-methyl-5,6,7,8-tetrahydro-thieno[2,3-d]azepine;
2-(4-Fluoro-phenyl)-5,6,7,8-tetrahydro-4H-thieno[2,3-d]azepine;
2-(2,5-Difluoro-phenyl)-5,6,7,8-tetrahydro-4H-thieno[2,3-d]azepine;
2-(3-Chloro-4-fiuoro-phenyl)-5,6,7,8-tetrahydro-4H-thieno[2,3-d]azepine;
2-(2,5-Dichloro-phenyl)-5,6,7,8-tetrahydro-4H-thieno[2,3-d]azepine;
2-(5-Fluoro-2-methoxy-phenyl)-5,6,7,8-tetrahydro-4H-thieno[2,3-d]azepine;
2-(3,4,5-Trimethoxy-phenyl)-5,6,7,8-tetrahydro-4H-thieno[2,3-d]azepine;
2-(4-Ethoxy-phenyl)-5,6,7,8-tetrahydro-4H-thieno[2,3-d]azepine;
2-(4-Ethyl-phenyl)-5,6,7,8-tetrahydro-4H-thieno[2,3-d]azepine;
2-(3-Methoxy-phenyl)-5,6,7,8-tetrahydro-4H-thieno[2,3-d]azepine;
2-Phenyl-5,6,7,8-tetrahydro-4H-thieno[2,3-d]azepine;
2-Naphthalene-1-yl-5,6,7,8-tetrahydro-4H-thieno[2,3-d]azepine;
2-Naphthalene-2-yl-5,6,7,8-tetrahydro-4H-thieno[2,3-d]azepine;
2-(2,6-Difluoro-phenyl)-5,6,7,8-tetrahydro-4H-thieno[2,3-d]azepine;
3-(2,6-Difluoro-phenyl)-5,6,7,8-tetrahydro-4H-thieno[2,3-d]azepine;
2-(2-Chloro-6-fluoro-benzyl)-5,6,7,8-tetrahydro-4H-thieno[2,3-d]azepine;
3-Bromo-2-(2-chloro-6-fluoro-benzyl)-5,6,7,8-tetrahydro-4H-thieno [2,3-d]azepine;
2-Bromo-3-methyl-5,6,7,8-tetrahydro-4H-thieno[2,3-d]azepine;
2-Bromo-3-methoxy-5,6,7,8-tetrahydro-4H-thieno[2,3-d]azepine;
2-Bromo-4-methyl-5,6,7,8-tetrahydro-4H-thieno[2,3-d]azepine;
2-Bromo-8-methyl-5,6,7,8-tetrahydro-4H-thieno[2,3-d]azepine;
5,6,7,8-Tetrahydro-4H-thieno[2,3-d]azepine-2-sulfonic acid dimethylamide;
3-Methyl-5,6,7,8-tetrahydro-4H-thieno[2,3-d]azepine-2-sulfonic acid dimethylamide;
2-Bromo-4,4a,5,6,7,8-hexahydro-3H-1-thia-6-aza-cyclopenta[cd]azulene;
2-Methyl-4,4a,5,6,7,8-hexahydro-3H-1-thia-6-aza-cyclopenta[cd]azulene;
2-Trifluoromethyl-5,6,7,8-tetrahydro-4H-thieno[2,3-d]azepine;
3-Bromo-2-trifluoromethyl-5,6,7,8-tetrahydro-4H-thieno [2,3-d]azepine; and
2-tert-Butyl-3-methoxy-5,6,7,8-tetrahydro-4H-thieno[2,3-d]azepine; or a
pharmaceutically acceptable salt thereof.

3. A compound selected from the group consisting of
2,3-Dichloro-5,6,7,8-tetrahydro-4H-thieno[2,3-d]azepine;
2-Bromo-3-chloro-5,6,7,8-tetrahydro-4H-thieno[2,3-d]azepine;
2-Bromo-3-methyi-5,6,7,8-tetrahydro-4H-thieno[2,3-d]azepine;
2-Bromo-3-methoxy-5,6,7,8-tetrahydro-4H-thieno[2,3-d]azepine;
2-Bromo-4-methyl-5,6,7,8-tetrahydro-4H-thieno[2,3-d]azepine;
2-Bromo-8-methyl-5,6,7,8-tetrahydro-4H-thieno[2,3-d]azepine;
5,6,7,8-Tetrahydro-4H-thieno[2,3-d]azepine-2-sulfonic acid dimethylamide;
3-Methyl-5,6,7,8-tetrahydro-4H-thieno[2,3-d]azepine-2-sulfonic acid dimethylamide;
2-Bromo-4,4a, 5,6,7, 8-hexahydro-3H-1-thia-6-aza-cyclopenta[cd]azulene;
2-Methyl-4,4a, 5,6,7,8-hexahydro-3H-1-thia-6-aza-cyclopenta[cd]azulene;
2-Trifluoromethyl-5,6,7,8-tetrahydro-4H-thieno[2,3-d]azepine;
3-Bromo-2-trifluoromethyl-5,6,7,8-tetrahydro-4H-thieno [2,3-d]azepine; and
2-tert-Butyl-3-methoxy-5,6,7,8-tetrahydro-4H-thieno[2,3-d]azepine; or a
pharmaceutically acceptable salt thereof.

4. A compound selected from the group consisting of:
2-(4-Trifluoromethoxy-phenyl)-5,6,7,8-tetrahydro-4H-thieno[2,3-d]azepine;
2-(2-Trifluoromethyl-phenyl)-5,6,7,8-tetrahydro-4H-thieno[2,3-d]azepine; and
2-(Pyrrolidine-1-sulfonyl)-5,6,7,8-tetrahydro-4H-thieno [2,3-diazepine; or a
pharmaceutically acceptable salt thereof.

5. A pharmaceutical composition comprising at least one compound of any of claims 1, 2, 3, or 4 and a pharmaceutically acceptable carrier.

* * * * *

UNITED STATES PATENT AND TRADEMARK OFFICE
CERTIFICATE OF CORRECTION

PATENT NO. : 7,718,647 B2
APPLICATION NO. : 11/170266
DATED : May 18, 2010
INVENTOR(S) : Bennani et al.

It is certified that error appears in the above-identified patent and that said Letters Patent is hereby corrected as shown below:

Column 77, line 5, please delete "tetrahydro-thieno" and insert --tetrahydro-4H-thieno--

Column 77, line 11, please delete "4-fiuoro-phenyl" and insert --4-fluoro-phenyl--

Column 78, line 15, please delete "3-methyi-5,6,7,8" and insert --3-methyl-5,6,7,8--

Column 78, line 45, please delete "[2,3-diazepine;" and insert --[2,3-d]azepine;--

Signed and Sealed this

Seventeenth Day of August, 2010

David J. Kappos
*Director of the United States Patent and Trademark Office*